(12) United States Patent
Kasper et al.

(10) Patent No.: US 10,329,315 B2
(45) Date of Patent: Jun. 25, 2019

(54) GLYCOSPHINGOLIPIDS AND METHODS OF USE THEREOF

(71) Applicants: The Brigham and Women's Hospital, Inc., Boston, MA (US); President and Fellows of Harvard College, Cambridge, MA (US)

(72) Inventors: Dennis L. Kasper, Brookline, MA (US); Dingding An, Brookline, MA (US); Sungwhan Oh, Brookline, MA (US); Richard S. Blumberg, Waltham, MA (US); Torsten Olszak, Munich (DE); Joana F. Neves, London (GB)

(73) Assignees: The Brigham and Women's Hospital, Inc., Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/435,222

(22) PCT Filed: Oct. 11, 2013

(86) PCT No.: PCT/US2013/064453
§ 371 (c)(1),
(2) Date: Apr. 13, 2015

(87) PCT Pub. No.: WO2014/059220
PCT Pub. Date: Apr. 17, 2014

(65) Prior Publication Data
US 2015/0252068 A1     Sep. 10, 2015

Related U.S. Application Data

(60) Provisional application No. 61/841,888, filed on Jul. 1, 2013, provisional application No. 61/717,446, filed on Oct. 23, 2012, provisional application No. 61/713,467, filed on Oct. 12, 2012.

(51) Int. Cl.
| | | |
|---|---|---|
| *C07H 15/04* | (2006.01) | |
| *A61K 31/7028* | (2006.01) | |
| *A61K 35/17* | (2015.01) | |
| *A61K 31/70* | (2006.01) | |
| *A61K 38/17* | (2006.01) | |
| *A61K 45/06* | (2006.01) | |
| *C12N 5/0783* | (2010.01) | |

(52) U.S. Cl.
CPC .......... *C07H 15/04* (2013.01); *A61K 31/70* (2013.01); *A61K 31/7028* (2013.01); *A61K 35/17* (2013.01); *A61K 38/177* (2013.01);

*A61K 45/06* (2013.01); *C12N 5/0646* (2013.01); *C12N 2502/11* (2013.01)

(58) Field of Classification Search
None
See application file for complete search history.

(56) References Cited

U.S. PATENT DOCUMENTS

| | | | |
|---|---|---|---|
| 4,981,618 A | | 1/1991 | Bruneteau et al. |
| 5,683,684 A | | 11/1997 | Montastier et al. |
| 5,869,034 A | | 2/1999 | Montastier et al. |
| 5,936,076 A | | 8/1999 | Higa et al. |
| 5,958,426 A | | 9/1999 | Moreau et al. |
| 6,071,884 A | | 6/2000 | Koezuka et al. |
| 7,682,614 B2 | | 3/2010 | Strober et al. |
| 7,906,488 B2 | | 3/2011 | Nieuwenhuizen |
| 7,968,529 B2 | | 6/2011 | Nieuwenhuizen |
| 2002/0164331 A1 | | 11/2002 | Exley et al. |
| 2002/0165170 A1 | | 11/2002 | Wilson et al. |
| 2006/0052316 A1 | | 3/2006 | Porcelli |
| 2006/0116331 A1 | | 6/2006 | Jiang et al. |
| 2006/0116332 A1 | | 6/2006 | Strober et al. |
| 2009/0239813 A1 | | 9/2009 | Cerundolo et al. |
| 2010/0104590 A1 | | 4/2010 | Kang et al. |
| 2010/0304467 A1 | | 12/2010 | Kodama et al. |
| 2014/0377291 A1* | | 12/2014 | Fischbach .............. C07H 15/04 424/184.1 |

FOREIGN PATENT DOCUMENTS

| | | |
|---|---|---|
| WO | WO 2001/57534 A2 | 8/2001 |
| WO | WO 2003/092615 A2 | 11/2003 |
| WO | WO 2012/018950 A1 | 2/2012 |
| WO | WO 2013/119857 A1 | 8/2013 |

OTHER PUBLICATIONS

Van Kaer et al., "Invariant NK T cells: potential for immunotherapeutic targeting with glycolipid antigens", Immunotherapy 2011, vol. 3, pp. 59-75.*
Supplementary European Search Report for Application No. 13845999.5 dated Feb. 26, 2016.
International Search Report and Written Opinion dated Feb. 13, 2014 for Application No. PCT/US2013/064453.

(Continued)

*Primary Examiner* — Michelle F. Paguio Frising
(74) *Attorney, Agent, or Firm* — Wolf, Greenfield & Sacks, P.C.

(57) ABSTRACT

The invention provides, inter alia, immunoinhibitory glycosphingolipids and immunoinhibitory alpha-galactosylceramides and compositions and preparations thereof, and methods of use thereof including in the treatment of conditions characterized by increased iNKT cells and/or activity.

18 Claims, 18 Drawing Sheets

(56) References Cited

OTHER PUBLICATIONS

International Preliminary Report on Patentability dated Apr. 23, 2015 for Application No. PCT/US2013/064453.

Altschul et al., Protein database searches using compositionally adjusted substitution matrices. FEBS J. Oct. 2005;272(20):5101-9.

An et al., Sphingolipids from a symbiotic microbe regulate homeostasis of host intestinal natural killer T cells. Cell. Jan. 16, 2014;156(1-2):123-33. doi: 10.1016/j.cell.2013.11.042.

An et al., Membrane sphingolipids as essential molecular signals for Bacteroides survival in the intestine. Proc Natl Acad Sci U S A. Mar. 15, 2011;108 Suppl 1:4666-71. doi: 10.1073/pnas.1001501107. Epub Sep. 20, 2010. Supplemental Information included.

Bezbradica et al., Distinct roles of dendritic cells and B cells in Va14Ja18 natural T cell activation in vivo. J Immunol. Apr. 15, 2005;174(8):4696-705.

Borrow et al., Innate immunity against HIV: a priority target for HIV prevention research. Retrovirology. Oct. 11, 2010;7:84. doi: 10.1186/1742-4690-7-84.

Braun et al., Natural killer T cells and atherosclerosis: form and function meet pathogenesis. J Innate Immun 2010;2(4):316-24. doi: 10.1159/000296915. Epub Mar. 17, 2010.

Bricard et al., A-galactosylceramide analogs with weak agonist activity for human iNKT cells define new candidate anti-inflammatory agents. PLoS One. Dec. 17, 2010;5(12):e14374. doi: 10.1371/journal.pone.0014374.

Brigl et al., Innate and cytokine-driven signals, rather than microbial antigens, dominate in natural killer T cell activation during microbial infection. J Exp Med. Jun. 6, 2011;208(6):1163-77. Doi: 10.1084/jem.20102555. Epub May 9, 2011. With Supplemental Material.

Brossay et al., Cutting Edge: Structural requirements for galactosylceramide recognition by CD1-restricted NK T cells. J Immunol. Nov. 15, 1998;161(10):5124-8.

Brown et al., Beta 2-microglobulin-dependent NK1.1+ T cells are not essential for T helper cell 2 immune responses. J Exp Med. Oct. 1, 1996;184(4):1295-304.

Comstock et al., Analysis of a capsular polysaccharide biosynthesis locus of Bacteroides fragilis. Infect Immun Jul. 1999;67(7):3525-32.

El Haj et al., Potential role of NKT regulatory cell ligands for the treatment of immune mediated colitis. World J Gastroenterol. Nov. 28, 2007;13(44):5799-804.

Fuss et al., Nonclassical CD1d-restricted NK T cells that produce IL-13 characterize an atypical Th2 response in ulcerative colitis. J Clin Invest. May 2004;113(10):1490-7.

Godfrey et al., New ways to turn on NKT cells. J Exp Med. Jun. 6, 2011;208(6):1121-5. doi: 10.1084/jem.20110983.

Haak et al., Hydroxylation of *Saccharomyces cerevisiae* ceramides requires Sur2p and Scs7p. J Biol Chem. Nov. 21, 1997;272(47):29704-10.

Heller et al., Oxazolone colitis, a Th2 colitis model resembling ulcerative colitis, is mediated by IL-13-producing NK-T cells. Immunity. Nov. 2002;17(5):629-38.

Kim et al., Heteroaromatic Moieties in the Sphingosine Backbone of α-Galactosylceramides for Noncovalent Interactions with CD1d. ACS Med Chem Lett. Jan. 10, 2012;3(2):151-4. doi: 10.1021/ml200278u.eCollection Feb. 9, 2012.

Lowther et al., Structural, mechanistic and regulatory studies of serine palmitoyltransferase. Biochem Soc Trans. Jun. 1, 2012;40(3):547-54. doi: 10.1042/BST20110769.

Matangkasombut et al., Natural killer T cells and the regulation of asthma. Mucosal Immunol. Sep. 2009;2(5):383-92. doi: 10.1038/mi.2009.96. Epub Jul. 8, 2009.

Matsuda et al., alpha-Galactosylceramide, a ligand of natural killer T cells, inhibits allergic airway inflammation. Am J Respir Cell Mol Biol. Jul. 2005;33(1):22-31. Epub Mar. 31, 2005.

Mazmanian et al., An immunomodulatory molecule of symbiotic bacteria directs maturation of the host immune system. Cell. Jul. 15, 2005;122(1):107-18.

Natori et al., Agelasphins, novel antitumor and immunostimulatory cerebrosides from the marine sponge *Agelas mauritianus*. Tetrahedron. Feb. 28, 1994;50(9):2771-2784.

Nichols et al., Unique lipids from a common human bacterium represent a new class of Toll-like receptor 2 ligands capable of enhancing autoimmunity. Am J Pathol. Dec. 2009;175(6):2430-8. doi: 10.2353/ajpath.2009.090544. Epub Oct. 22, 2009.

Noda et al., Two Novel Galactosylceramides from Marphysa sanguinea. Tetrahedron Letters. 1992;33(49):7527-7530.

Olszak et al., Microbial exposure during early life has persistent effects on natural killer T cell function. Science. Apr. 27, 2012;336(6080):489-93. doi: 10.1126/science.1219328. Epub Mar. 22, 2012.

Paget et al., Activation of invariant NKT cells by toll-like receptor 9-stimulated dendritic cells requires type I interferon and charged glycosphingolipids. Immunity. Oct. 2007;27(4):597-609 Epub Oct. 18, 2007.

Raghuraman et al., IFN-beta-mediated up-regulation of CD1d in bacteria-infected APCs. J Immunol. Dec. 1, 2006;177(11):7841-8.

Rai et al., Synthesis of the glycosphingolipid beta-galactosyl ceramide and analogues via olefin cross metathesis. J Org Chem. Sep. 30, 2005;70(20):8228-30.

Sada-Ovalle et al., Alpha-galactosylceramide as a therapeutic agent for pulmonary *Mycobacterium tuberculosis* infection. Am J Respir Crit Care Med. Sep. 15, 2010;182(6):841-7. doi: 10.1164/rccm.200912-1921OC. Epub May 27, 2010.

Salio et al., Modulation of human natural killer T cell ligands on TLR-mediated antigen-presenting cell activation. Proc Natl Acad Sci U S A. Dec. 18, 2007;104(51):20490-5. Epub Dec. 11, 2007.

Schiechl et al., Tumor development in murine ulcerative colitis depends on MyD88 signaling of colonic F4/80+CD11b(high)Grl(low) macrophages. J Clin Invest. May 2011;121(5):1692-708. doi: 10.1172/JCI42540. Epub Apr. 25, 2011.

Schmieg et al., Glycolipid presentation to natural killer T cells differs in an organ-dependent fashion. Proc Natl Acad Sci U S A. Jan. 25, 2005;102(4):1127-32. Epub Jan. 11, 2005.

Sidobre et al., The V alpha 14 NKT cell TCR exhibits high-affinity binding to a glycolipid/CD1d complex. J Immunol. Aug. 1, 2002;169(3):1340-8.

Sidobre et al., The T cell antigen receptor expressed by Valpha14i NKT cells has a unique mode of glycosphingolipid antigen recognition. Proc Natl Acad Sci U S A. Aug. 17, 2004;101(33):12254-9. Epub Aug. 10, 2004.

Sköld et al., Interplay of cytokines and microbial signals in regulation of CD1d expression and NKT cell activation. J Immunol. Sep. 15, 2005;175(6):3584-93.

Strachan, Hay fever, hygiene, and household size. BMJ. Nov. 18, 1989;299(6710):1259-60.

Wieland Brown et al., Production of α-galactosylceramide by a prominent member of the human gut microbiota. PLoS Biol. Jul. 2013;11(7):e1001610. doi: 10.1371/journal.pbio.1001610. Epub Jul. 16, 2013.

Wingender et al., Intestinal microbes affect phenotypes and functions of invariant natural killer T cells in mice. Gastroenterology. Aug. 2012;143(2):418-28. doi: 10.1053/j.gastro.2012.04.017. Epub Apr. 19, 2012.

Yamamura, [Synthetic glycolipid ligands as novel therapeutics for multiple sclerosis]. Rinsho Shinkeigaku. Nov. 2005;45(11):909-11. Review. Japanese. Abstract Only.

Yoshioka et al., Role of natural killer T cells in the mouse colitis-associated colon cancer model. Scand J Immunol. Jan. 2012;75(1):16-26. doi: 10.1111/j.1365-3083.2011.02607.x.

Zeng et al., Activation of natural killer T cells in NZB/W mice induces Th1-type immune responses exacerbating lupus. J Clin Invest. Oct. 2003;112(8):1211-22.

Zhang et al., Beta 2-microglobulin-dependent T cells are dispensable for allergen-induced T helper 2 responses. J Exp Med. Oct. 1, 1996;184(4):1507-12.

Zigmond et al., Beta-glucosylceramide: a novel method for enhancement of natural killer T lymphoycte plasticity in murine models of immune-mediated disorders. Gut. Jan. 2007;56(1):82-9.

(56) References Cited

OTHER PUBLICATIONS

Akbari et al., Essential role of NKT cells producing IL-4 and IL-13 in the development of allergen-induced airway hyperreactivity. Nat Med. May 2003;9(5):582-8. Epub Mar. 31, 2003.
Bäckhed et al., Host-bacterial mutualism in the human intestine. Science. Mar. 25, 2005;307(5717):1915-20.
Banchet-Cadeddu et al., The stimulating adventure of KRN 7000. Org Biomol Chem. May 7, 2011;9(9):3080-104. doi: 10.1039/c0ob00975j. Epub Mar. 11, 2011.
Burrows et al., NKT cells turn ten. Nat Immunol. Jul. 2009;10(7):669-71. doi: 10.1038/ni0709-669.
Chow et al., Host-bacterial symbiosis in health and disease. Adv Immunol. 2010;107:243-74. doi: 10.1016/B978-0-12-381300-8.00008-3.
Cohen et al., Antigen Presentation by CD1 Lipids, T Cells, and NKT Cells in Microbial Immunity. Adv Immunol. 2009;102:1-94. doi: 10.1016/S0065-2776(09)01201-2.
Fernandez et al., Activation of invariant Natural Killer T lymphocytes in response to the Beta-galactosylceramide analogue KRN7000 encapsulated in PLGA-based nanoparticles and microparticles. International Journal of Pharmaceutics. 2012;423:45-54.
Hancock et al., Designer enzymes for glycosphingolipid synthesis by directed evolution. Nat Chem Biol. Jul. 2009;5(7):508-14. doi: 10.1038/nchembio.191.
Honda et al., The microbiome in infectious disease and inflammation. Annu Rev Immunol. 2012;30:759-95. doi: 10.1146/annurev-immunol-020711-074937. Epub Jan. 6, 2012.
Isolauri et al., Obesity—extending the hygiene hypothesis. Nestle Nutr Workshop Ser Pediatr Program. 2009;64:75-85; discussion 85-9, 251-7. doi: 10.1159/000235784. Epub Aug. 19, 2009.
Kato et al., Sphingolipid composition in *Bacteroides* species. Anaerobe. Apr. 1995;1(2):135-9.
Kawano et al., CD1d-restricted and TCR-mediated activation of valpha14 NKT cells by glycosylceramides. Science. Nov. 28, 1997;278(5343):1626-9.
Kinjo et al., Natural killer T cells recognize diacylglycerol antigens from pathogenic bacteria. Nat Immunol. Sep. 2006;7(9):978-86. Epub Aug. 20, 2006.
Kinjo et al., Recognition of bacterial glycosphingolipids by natural killer T cells. Nature. Mar. 24, 2005;434(7032):520-5.
Kronenberg et al., Toward an understanding of NKT cell biology: progress and paradoxes. Annu Rev Immunol. 2005;23:877-900.
Liu et al., Total synthesis of α-1C-galactosylceramide, an immunostimulatory C-glycosphingolipid, and confirmation of the stereochemistry in the first-generation synthesis. J Org Chem. Nov. 4, 2011;76(21):8588-98. doi: 10.1021/jo201450s. Epub Oct. 4, 2011.
Matsuda et al., CD1d-restricted iNKT cells, the 'Swiss-Army knife' of the immune system. Curr Opin Immunol. Jun. 2008;20(3):358-68. doi: 10.1016/j.coi.2008.03.018. Epub May 22, 2008.
Mattner et al., Exogenous and endogenous glycolipid antigens activate NKT cells during microbial infections. Nature. Mar. 24, 2005;434(7032):525-9.
Mazmanian et al., A microbial symbiosis factor prevents intestinal inflammatory disease. Nature. May 29, 2008;453(7195):620-5. doi: 10.1038/nature07008.
Numata et al., Therapeutic effect of repeated natural killer T cell stimulation in mouse cholangitis complicated by colitis. Dig Dis Sci. Oct. 2005;50(10):1844-51.
Olsen et al., Sphingolipids in Bacteria and Fungi. Anaerobe. Apr. 2001;7(2):103-112.
Peternel et al., Immunopathogenesis of psoriasis: focus on natural killer T cells. J Eur Acad Dermatol Venereol. Oct. 2009;23(10):1123-7. doi: 10.1111/j.1468-3083.2009.03292.x. Epub Apr. 30, 2009.
Rossjohn et al., Recognition of CD1d-restricted antigens by natural killer T cells. Nat Rev Immunol. Dec. 2012;12(12):845-57. doi: 10.1038/nri3328. Epub Nov. 16, 2012.
Umetsu et al., Regulatory T cells control the development of allergic disease and asthma. J Allergy Clin Immunol. Sep. 2003;112(3):480-7.
Wills-Karp et al., The germless theory of allergic disease: revisiting the hygiene hypothesis. Nat Rev Immunol. Oct. 2001;1(1):69-75.
Wollenweber et al., Nature, type of linkage, quantity, and absolute configuration of (3-hydroxy) fatty acids in lipopolysaccharides from Bacteroides fragilis NCTC 9343 and related strains. J Bacteriol. Dec. 1980;144(3):898-903.
Zigmond et al., NKT lymphocyte polarization determined by microenvironment signaling: a role for CD8+lymphocytes and beta-glycosphingolipids. J Autoimmun. Sep. 2008;31(2):188-95. doi: 10.1016/j.jaut.2008.07.003. Epub Aug. 16, 2008.

\* cited by examiner m=11~15, l=0-2, n+l=13~17

GLYCOSPHINGOLIPIDS AND METHODS OF USE THEREOF

RELATED APPLICATIONS

This application is a national stage filing under 35 U.S.C. § 371 of International Application No. PCT/US2013/064453 filed Oct. 11, 2013, which was published under PCT Article 21(2) in English, and which claims the benefit of U.S. Provisional Application No. 61/713,467 filed Oct. 12, 2012, U.S. Provisional Application No. 61/717,446 filed Oct. 23, 2012, and U.S. Provisional Application No. 61/841,888, filed Jul. 1, 2013, the entire contents of each of which are incorporated by reference herein.

FEDERALLY SPONSORED RESEARCH

This invention was made with U.S. Government support under grant number R21-AI090102 awarded by the National Institutes of Health. The U.S. Government has certain rights in this invention.

BACKGROUND OF INVENTION

Invariant natural killer T (iNKT) cells are important in both innate and the adaptive immunity. Once activated, they release massive amounts of inflammatory cytokines and play an important pro-inflammatory role in a range of disease processes, including autoimmune diseases, infectious diseases, and cancer. Commensal microbiota can modulate iNKT cell numbers in vivo, including in the gut and in the lungs. As a result, conventionally colonized mice (e.g., the normal mouse microbiome) have significantly fewer iNKT cells in these two compartments compared to germ-free mice. When challenged in iNKT cell-dependent asthma and ulcerative colitis models, the conventional mice are protected while the germ-free mice had severe disease phenotypes, suggesting that low numbers of iNKT cells in the colon and lung are associated with resistance to experimental colitis and asthma.

SUMMARY OF INVENTION

The invention is premised on the unexpected finding of certain glycosphingolipids having immunoinhibitory activity. One particularly unexpected finding of the invention is the discovery of a class of glycosphingolipids that inhibit the activity of invariant natural killer T (iNKT) cells. The immune inhibitory class of glycosphingolipids are characterized as a subset of alpha-galactosylceramides having particular structural features. It has been found that these molecules are able to inhibit iNKT activation and reduce iNKT cell numbers. This finding is particularly surprising since alpha-galactosylceramides have been previously characterized as immune stimulating molecules and their ability to activate NKT cells has been reported. Thus the discovery of a subclass of these molecules that exists naturally and is able to inhibit iNKT cells is unexpected. The invention therefore contemplates the use of these molecules in treating or preventing altogether conditions characterized by increased iNKT cell numbers and/or activity.

Thus, in one embodiment, the invention provides an isolated immune inhibitory alpha-galactosylceramide (referred to herein as alpha-GC for brevity). The isolated alpha-GC comprises a galactose head group and a ceramide which in turn comprises a fatty acid chain and a sphingosine, sphinganine or phytosphingosine chain. The differences between these chains are shown herein. This latter chain of the ceramide moiety is referred to herein as the sphingosine chain for the sake of brevity and convenience, but it is to be understood that it can be sphinganine or phytosphingosine as well.

In some embodiments, the isolated alpha-GC comprises a fatty acid or sphingosine chain length equal to or less than 20 carbons. In some embodiments, the fatty acid or sphingosine chain length is 15, 16, 17, 18 or 19 carbons. In some embodiments, the fatty acid or sphingosine chain length is 17 carbons. In some embodiments, each of the fatty acid and sphingosine chain lengths is 17 carbons.

In some embodiments, the isolated alpha-GC comprises a fatty acid chain having one or more hydroxyl groups. In some embodiments, the fatty acid chain has one hydroxyl group. In some embodiments, the fatty acid chain has a hydroxyl group on C2 (sometimes referred to as C2' to denote position on the fatty acid chain rather than the sphingosine chain). In some embodiments, the fatty acid chain has a hydroxyl group on C3 (sometimes referred to as C3' to denote position on the fatty acid chain rather than the sphingosine chain). In some embodiments, the sphingosine chain has a hydroxyl group at the C4 position (sometimes referred to as C4' to denote position on the fatty acid chain rather than the sphingosine chain). In some embodiments, the isolated alpha-GC comprises a sphingosine chain having one or more hydroxyl groups. Hydroxyls on the sphingosine chain can occur at positions C2, C3 or C4, in some embodiments.

In some embodiments, the isolated alpha-GC comprises a fatty acid or a sphingosine chain that is branched. In some embodiments, the fatty acid or sphingosine chain is branched at the omega-2 (iso) position or omega-3 (ante-iso) position. In some embodiments, the fatty acid or sphingosine chain comprises a terminal isomethyl or an ante-isomethyl group. In some embodiments, each of the fatty acid or sphingosine chains comprises a terminal isomethyl or an ante-isomethyl group.

In some embodiments, the isolated alpha-GC is obtained from a naturally occurring source. Naturally occurring sources are *Bacteroides* species such as but not limited to *Bacteroides fragilis*. In some embodiments, the isolated alpha-GC is produced synthetically. Synthetic forms of alpha-GC may be structurally identical to the naturally occurring form but may be provided in differing degrees of purity, including 50% or more, 60% or more, 70% or more, 80% or more, 90% or more, 95% or more, 99% or more, or 100% purity. In some embodiments, the isolated alpha-GC is produced synthetically and is not structurally identical to a naturally occurring form (i.e., it is not naturally occurring intending that it is not found in nature).

In some embodiments, a carbon of either or both the fatty acid or the sphingosine that is attached to a hydroxyl group exhibits chirality (and is therefore referred to as a chiral carbon). Such chirality may be R-chirality or S-chirality.

In some embodiments, the fatty acid C2 position has R-chirality. In some embodiments, the fatty acid C2 position has S-chirality. In some embodiments, the isolated alpha-GC is present as a racemic mixture at the fatty acid C2 position. In some embodiments, the fatty acid C3 position has R-chirality. In some embodiments, the fatty acid C3 position has S-chirality. In some embodiments, the isolated alpha-GC is present as a racemic mixture at the fatty acid C3 position. In some embodiments, the fatty acid C4 position has R-chirality. In some embodiments, the fatty acid C4 position has S-chirality. In some embodiments, the isolated alpha-GC is present as a racemic mixture at the fatty acid C4 position.

In some embodiments, the sphingosine C2 position has R-chirality. In some embodiments, the sphingosine C2 position has S-chirality. In some embodiments, the isolated alpha-GC is present as a racemic mixture at the sphingosine C2 position. In some embodiments, the sphingosine C3 position has R-chirality. In some embodiments, the sphingosine C3 position has S-chirality. In some embodiments, the isolated alpha-GC is present as a racemic mixture at the sphingosine C3 position. In some embodiments, the sphingosine C4 position has R-chirality. In some embodiments, the sphingosine C4 position has S-chirality. In some embodiments, the isolated alpha-GC is present as a racemic mixture at the sphingosine C4 position.

The isolated alpha-GC may have the following structure

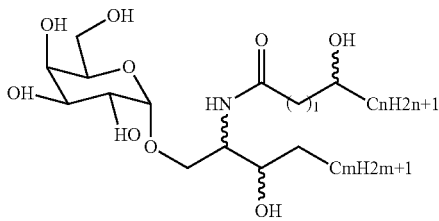

wherein m=11~15, 1=0-2, and n+1=13~17.

In another aspect, the invention provides a composition comprising any of the foregoing isolated alpha-GC. In some embodiments, the composition is sterile. In some embodiments, the composition is intended for in vivo use in human or animal subjects. In some embodiments, the composition is intended for in vitro use.

In another aspect, the invention provides a pharmaceutical composition comprising any of the foregoing isolated alpha-GC. The pharmaceutical composition may further comprise a pharmaceutically acceptable carrier or it may be combined with a pharmaceutically acceptable carrier (e.g., it may be a lyophilized form of the isolated alpha-GC).

In some embodiments, the isolated alpha-GC is formulated for delivery to lungs (e.g., with an atomizer or nebulizer). In some embodiments, the isolated alpha-GC is formulated for delivery to the gut or colon.

In some embodiments, the composition or pharmaceutical composition further comprises another agent such as but not limited to an active agent such as an immunosuppressant or an anti-inflammatory agent. The other active agent may be one used to treat or prevent an inflammatory condition such as an autoimmune disease or asthma.

It is to be understood that the isolated alpha-GC may be provided in a pure form or as a mixture of different alpha-GC. The invention contemplates that the composition may be stereochemically pure or it may be a racemic mixture at one or more positions in the alpha-GC.

In another aspect, the invention provides a method comprising administering to a subject having or at risk of developing a condition characterized by increased iNKT cell numbers or activity any of the foregoing isolated alpha-GC in an effective amount to decrease iNKT cell numbers or activity.

In some embodiments, the condition is an inflammatory condition. In some embodiments, the condition is asthma. In some embodiments, the condition is an autoimmune disease. In some embodiments, the condition is inflammatory bowel disease. In some embodiments, the condition is colitis (e.g., ulcerative colitis). In some embodiments, the condition is systemic lupus erythematosus (i.e., lupus). In some embodiments, the condition is multiple sclerosis. In some embodiments, the condition is arthritis.

In some embodiments, the isolated alpha-GC is administered locally such as to the lungs or to the colon or gut. Local administration to the lungs may be carried out via nebulization, as an example. In some embodiments, the isolated alpha-GC is administered systemically.

In some embodiments, the subject is human. In some embodiments, the subject is less than 5 years of age, less than 1 year of age, less than 6 months of age, or less than 1 month of age. In some embodiments, the subject is a pregnant subject and optionally is at high risk of developing a condition characterized by increased iNKT cell numbers or activity. In some embodiments, the subject is a female subject of child-bearing age (e.g., in humans, approximately 15-55 years of age), and optionally is at increased (i.e., above-normal) risk of developing a condition characterized by increased iNKT cell numbers or activity.

In some embodiments, the subject is administered a second active agent such as an immunosuppressant or an anti-inflammatory agent.

In some embodiments, the method further comprises identifying a subject having or at risk (including increased risk) of developing the condition.

In another aspect, the invention provides a method comprising contacting CD1d-expressing antigen presenting cells or iNKT activating antigen presenting cells with any of the foregoing isolated alpha-GC, and contacting the antigen presenting cells with activated iNKT cells.

In some embodiments, the antigen presenting cells are dendritic cells.

In some embodiments, the antigen presenting cells are contacted with the isolated alpha-GC in vitro. In some embodiments, the antigen presenting cells, loaded with alpha-GC, are contacted with the activated iNKT cells in vivo.

In another aspect, the invention provides a method comprising contacting isolated CD1d protein loaded with (i.e., bound to) any of the foregoing isolated alpha-GC with activated iNKT cells. Isolated CD1d protein refers to CD1d that is not provided in the context of a cell such as an antigen-presenting cell. Contacting may occur in vitro or in vivo.

In another aspect, the invention provides a method comprising administering to a subject having or at risk of developing a condition characterized by increased iNKT cell numbers or activity any of the foregoing isolated alpha-GC bound to CD1d protein in an effective amount to decrease iNKT cell numbers or activity, wherein the CD1d protein is isolated (i.e., not provided in a cell-bound form). The CD1d protein may be provided as a CD1 d tetramer.

Other advantages and novel features of the present invention will become apparent from the following detailed description of various non-limiting embodiments of the invention when considered in conjunction with the accompanying Figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying Figures are not intended to be drawn to scale. For purposes of clarity, not every component may be labeled in every Figure. In the Figures:

FIG. 1B shows the dynamics of colonic LP total iNKT cell numbers in germ free (GF) mice, specific pathogen free (SPF) mice, wild-type *B. fragilis* (BFWT) and delta SPT mutant (BFΔSPT) mono-colonized mice. FIG. 1C shows the dynamics of colonic LP iNKT cells as a percentage of total CD3+ cells in GF mice, SPF mice, BFWT and BFΔSPT mono-colonized mice.

FIG. 1G shows by intracellular staining of Ki-67 protein from birth to 9 weeks of age. FIG. 1H shows by the BrdU method at 8 days of age that the proliferation rate of colonic LP iNKT cells at the neonatal stage was higher in GF and BFΔSPT mice than in SPF and BFWT mice.

FIG. 2A shows that *B. fragilis* sphingolipids do not activate iNKT cell line in an in vitro co-culture with bone marrow dendritic cells (BMDCs). FIG. 2B shows the ability of glycosphingolipids (GL-SL) to antagonize the stimulatory effects of KRN7000 on iNKT cells in vitro in comparison to ceramides (Cer-SL) and phosphoethanolamine-sphingolipids (PE-SL).

FIG. 3A shows lipidomic analysis of the GL-SL fraction, identifying chain length variants of *B. fragilis* glycosphingolipids. FIG. 3B shows a tandem MS spectrum of GL-SL peak 2, showing characteristic fragmentation of hexose-conjugated ceramide. FIG. 3C is a HPAEC analysis of GL-SL peak 2 hydrolysate, assigning conjugated hexose as galactose. FIG. 3D is a proton 1D NMR analysis profile of GL-SL peak 2. These analyses indicate that peak 2 is an alpha-GC-C17. This alpha-GC-C17 is referred to herein as alpha-GC-Bf717 and "peak 2" interchangeably.

DETAILED DESCRIPTION OF INVENTION

Figure 1A:
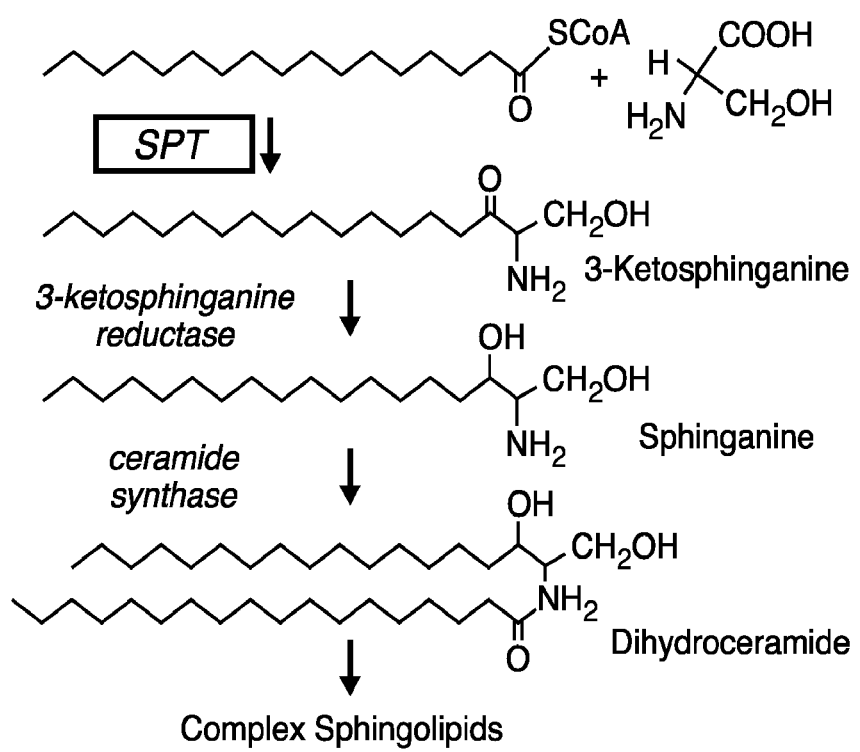
FIG. 1A shows a sphingolipid biosynthetic pathway. Indicated in the box is serine palmitoyltransferase (SPT), the first committed enzyme in sphingolipid biosynthesis.

The invention provides compositions and methods of use of immune inhibitory alpha-galactosylceramides (alpha-GC). As described in the Examples, in accordance with the invention, it was expectedly found that a subclass of alpha-GC are immunoinhibitory rather than immunostimulatory as previously described. These immunoinhibitory alpha-GC were obtained from *Bacteroides fragilis* (*B. fragilis*). The invention contemplates naturally sourced (i.e., obtained from a naturally occurring source) as well as synthetic forms of the immunoinhibitory alpha-GC, including synthetic non-naturally occurring forms of the alpha-GC. The naturally occurring source may be species within the *Bacteroides* genus and Bacteroidetes phylum which contain sphingolipids-bearing membranes. An example is *B. fragilis*. Other sources are contemplated as well and the invention is not limited by the source of the alpha-GC or other immunoinhibitory preparations, such as the GL-SL immunoinhibitory preparations, of the invention.

These immunoinhibitory alpha-GC were discovered in the process of attempting to identify specific microbial products in the normal mouse microbiome that modulate iNKT cell accumulation in the colon and lung. In accordance with the invention, a glycosphingolipid containing preparation derived from the commensal bacterium *B. fragilis* was obtained and found to modulate iNKT cell numbers and activity. This preparation contained, inter alia, an alpha-galactosylceramide having a 17 carbon ceramide chain length (alpha-GC-C17Cer). It was further found that alpha-GC-C17Cer could function as an iNKT cell antagonist that modulates iNKT cell activation by other endogenous or exogenous ligands. Since the usual response of iNKT cells is to produce pro-inflammatory cytokines, alpha-GC-C17Cer was shown to have anti-inflammatory function. The Examples provide in vitro and in vivo evidence that alpha-GC-C17Cer is capable of reducing the inflammatory cytokine release, i.e., IFN-gamma, by iNKT cells.

In order to study the activity of the *B. fragilis* fractions and the isolated alpha-GC, we constructed a mutant of *B. fragilis* that is incapable of producing any sphingolipids, including alpha-GC-C17Cer. When groups of germ-free mice were mono-colonized with either the wild-type or the sphingolipid-deficient mutant *B. fragilis*, colonic iNKT cell numbers were 2-3 fold higher in the mice mono-colonized with sphingolipid-deficient mutant than the mice colonized with type bacteria. When challenged in the experimental colitis model, the mice mono-colonized with the sphingolipid-deficient mutant bacteria showed a severe colitis phenotype while the mice mono-colonized with wild-type bacteria were protected. These data are consistent with our comparison of mice that are conventionally colonized with sphingolipid-bearing bacteria or germ free mice that are similar to the sphingolipid-deficient mice in terms of susceptibility to colitis and numbers of iNKT cells in the colon.

We also treated sphingolipid-deficient mutant mono-colonized mice with the purified aGC-C17Cer and this treatment decreased the colonic iNKT cell number to the level of the wild-type mono-colonized mice. The purified glycosphingolipid complemented the phenotype of the mutant bacteria colonized mice. The immunoinhibitory aGC-C17Cer can therefore be used as a therapeutic agent to inhibit iNKT activation and/or cell number and to treat iNKT cell-mediated diseases as described in greater detail herein.

The invention therefore provides immunoinhibitory alpha-GC, compositions thereof, and in vitro and in vivo methods of use thereof.

Immunoinhibitory Alpha-Galactosylceramides (Alpha-GC) and Glycosphingolipid Preparations The invention therefore provides immunoinhibitory molecules and preparations. Immunoinhibitory preparations are compositions obtained (or derived) from naturally occurring sources, such as a *Bacteroides* species such as but not limited to *B. fragilis*. These preparations may comprise a mixture of immunoinhibitory molecules, optionally together with other moieties that may or may not be immunomodulatory. An example of an immunoinhibitory preparation is a glycosphingolipid-enriched preparation obtained from a naturally occurring source such as a *Bacteroides* species such as but not limited to *B. fragilis*. The preparation may comprise the immunoinhibitory alpha-GC of the invention. Preparations, whether produced synthetically or obtained from naturally occurring sources, may comprise immunoinhibitory glycosphingolipids and/or alpha-GC at varying degrees of purity, including for example 50% or more, 60% or more, 70% or more, 80% or more, 90% or more, 95% or more, 99% or more, or 100% purity. Purity may be determined by performing an chemical analysis on the preparation such as a mass spec or an HPLC in order to determine if other components are present in the preparation and to quantitate such components relative to the desired immunoinhibitory glycosphingolipids and/or alpha-GC. Purity may be expressed in terms of [weight of the immunoinhibitory glycosphingolipids and/or alpha-GC] over [weight of the preparation], preferably where the preparation is dried, lyophilized, and the like.

As used herein, an immunoinhibitory molecule or preparation intends that the molecule or preparation is able to inhibit or reduce iNKT cell numbers and/or iNKT cell activity. It is therefore to be understood that the immunoinhibitory molecules and preparations of the invention are immunoinhibitory in the context of activated iNKT cells. For example, the molecules and preparations are able to reduce the number and activity of iNKT cells, including activated iNKT cells, and/or are able to prevent the activation of iNKT cells in the presence of an agent that stimulates iNKT cells such as an immunostimulatory alpha-GC such as for example KRN7000. Thus, in some instances, the immunoinhibitory alpha-GC of the invention are able to compete and/or interfere with immunostimulatory alpha-GC such as KRN7000, thereby preventing or reducing the degree of stimulation that would otherwise occur in the presence of KRN7000 alone. Where iNKT cell numbers and activity levels are normal (e.g., the levels in a subject that does not have an inflammatory condition and/or is not at elevated risk of developing an inflammatory condition (as a result of heredity, for example)), then the immunoinhibitory molecules and preparations may manifest no immunoinhibitory effect essentially because there is no observable background iNKT cell based immune stimulation. In some instances, however, they may manifest no immunoinhibitory effect in the short term but may function to prevent immunostimulatory in the long term by rendering a subject or the offspring of a subject, such as an infant or a child, resistant to future aberrant iNKT cell based immunostimulation.

Assays for measuring iNKT cell numbers are known in the art. Assays for measuring iNKT cell activity are also known in the art and are described in the Examples. These assays include cytokine production assays such as IFN-gamma, IL-2 and IL-4 production assays. In some instances, a reduction or inhibition of iNKT cell numbers and/or iNKT cell activity is measured by symptoms that result from increased numbers of iNKT cells and/or increased iNKT cell activity. Such symptoms include the symptoms associated with inflammatory conditions such as but not limited to autoimmune diseases. An exemplary but not limiting inflammatory condition is asthma. An exemplary but not limiting autoimmune disease is colitis.

As described in greater detail in the Examples, *B. fragilis* sphingolipids were extracted and fractionated using a silica column. That exemplary and non-limiting method for obtaining such sphingolipids is described briefly here. Overnight-grown *B. fragilis* 9343 strain were centrifuged, washed, and total lipids were extracted with a modified Bligh-Dyer method (chloroform:methanol:water (2:1:0.8) mixture, overnight incubation). Phases were separated using additional chloroform and water, and then the lower organic phase was collected and evaporated in preparation for loading onto a normal-phase silica column Lipids of different polarity were fractionated by stepwise elution with organic solvents of increasing polarity. Sphingolipids with different head groups, such as ceramides (Cer-SL), phosphoethanolamine-sphingolipids (PE-SL) and glycosphingolipids (GL-SL) were obtained. None of these fractions were capable of stimulating iNKT cells, especially in comparison to the positive control KRN7000, an alpha-galactosylceramide having a long (C26) ceramide chain. However, when these same fractions were tested for their ability to antagonize the iNKT cell stimulatory activity of KRN7000, only the GL-SL fraction showed appreciable antagonistic activity. Further analysis revealed that antagonistic activity was dose-dependent.

The GL-SL fraction was then analyzed by LC-MS/MS spectrometry and found to contain, inter alia, glycosphingolipids having C16, C17, C18 and C19 aliphatic sphingosine chains. These glycosphingolipids accounted for approximately 99% of the total GL-SL fraction by molar abundance. Pure glycosphingolipids from the GL-SL fraction were further isolated by RP-HPLC using a C18 column (Agilent Zorbax C18).

Additional analyses were carried out to determine the structure of a specific purified C17 *B. fragilis* glycosphingolipids. A composition assay with ion chromatography (DIONEX) indicated that the sugar head group is galactose. 1H NMR analyses indicated that (1) the linkage between the galactose and the ceramide is an alpha linkage, and (2) terminal branching of acyl chains is present in either iso- or anteiso-forms. Accordingly, certain immunoinhibitory alpha-GC species of the invention comprise ceramide moieties each having a fatty acid chain and a sphingosine chain. For the sake of brevity and convenience, the latter chain is referred to herein as the sphingosine chain. It is however to be appreciated that this chain may be a sphingosine, dihydrosphingosine (sphinganine) or a phytosphingosine as all have been found to occur in *B. fragilis*. The structure of these chains is as follows:

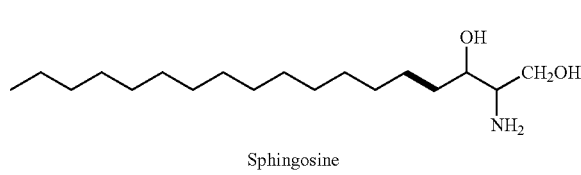

Sphingosine

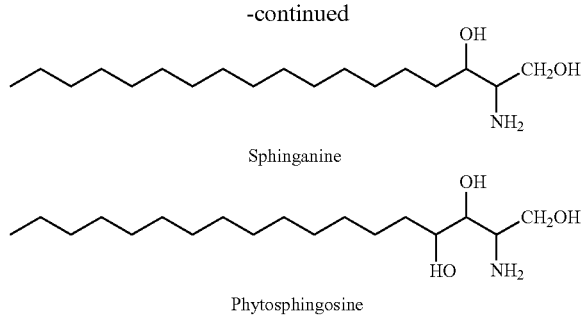

Sphinganine

Phytosphingosine

Figure 3A:
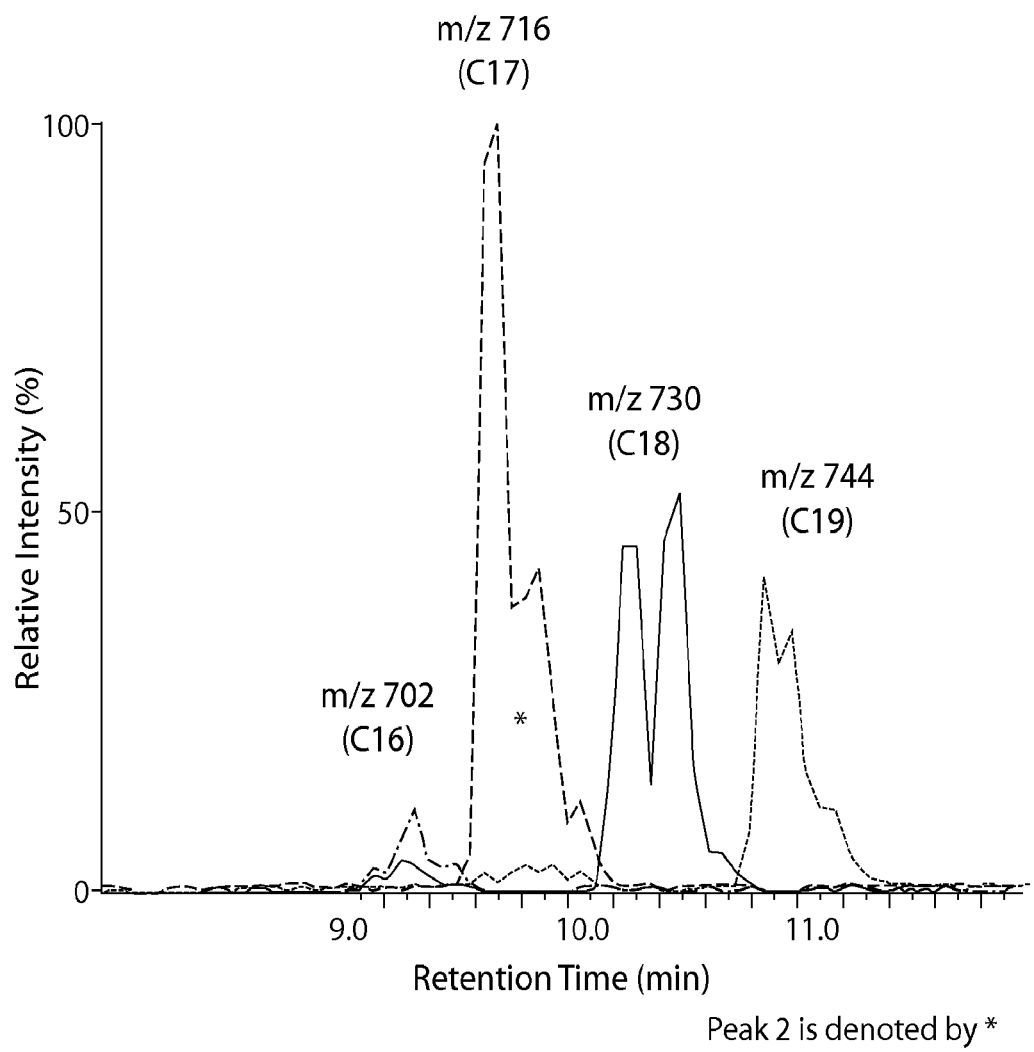
FIGS. 3A-D show analytical profiles of the GL-SL fraction and GL-SL subfractions.
Figure 3B:
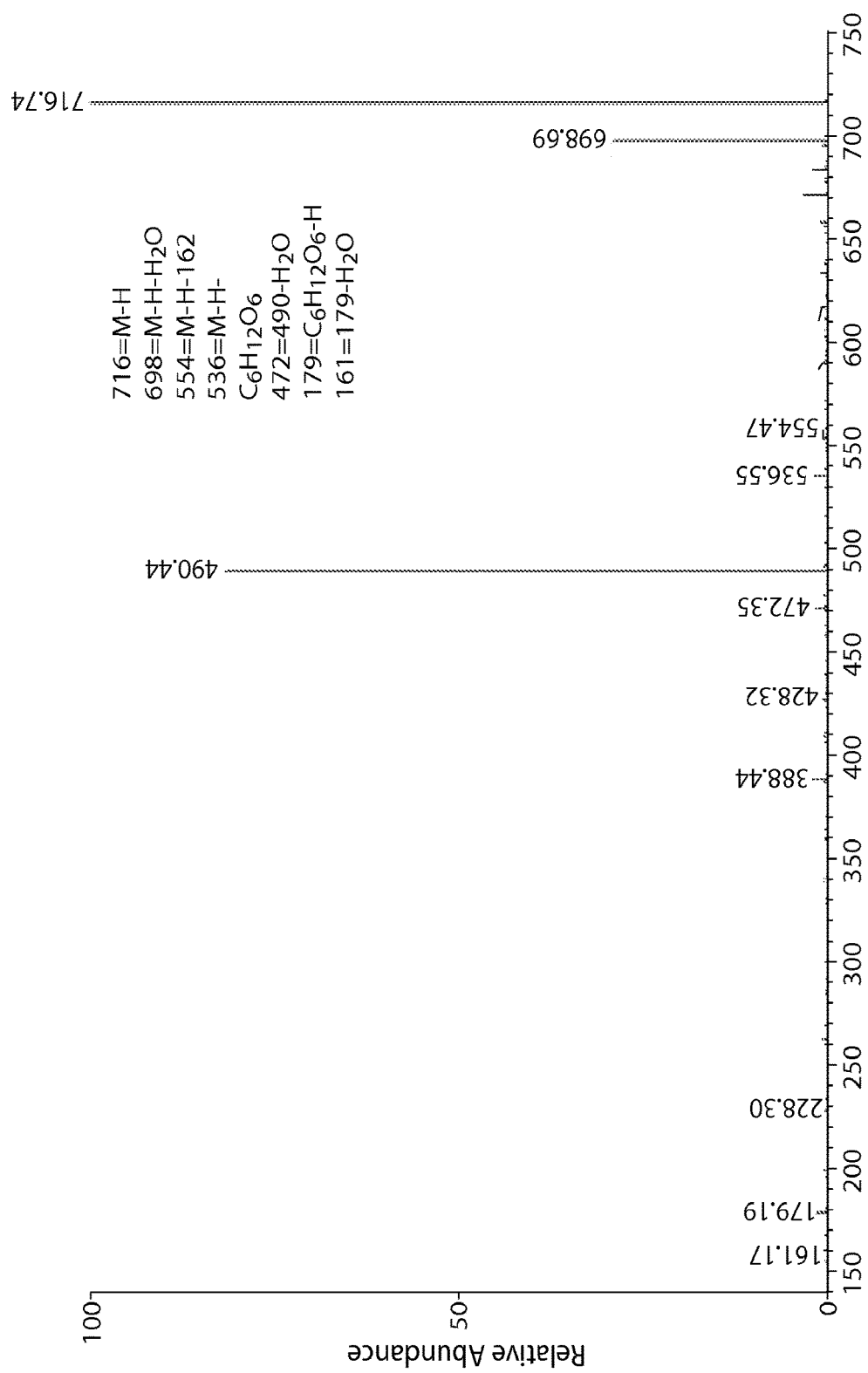
Figure 3C:
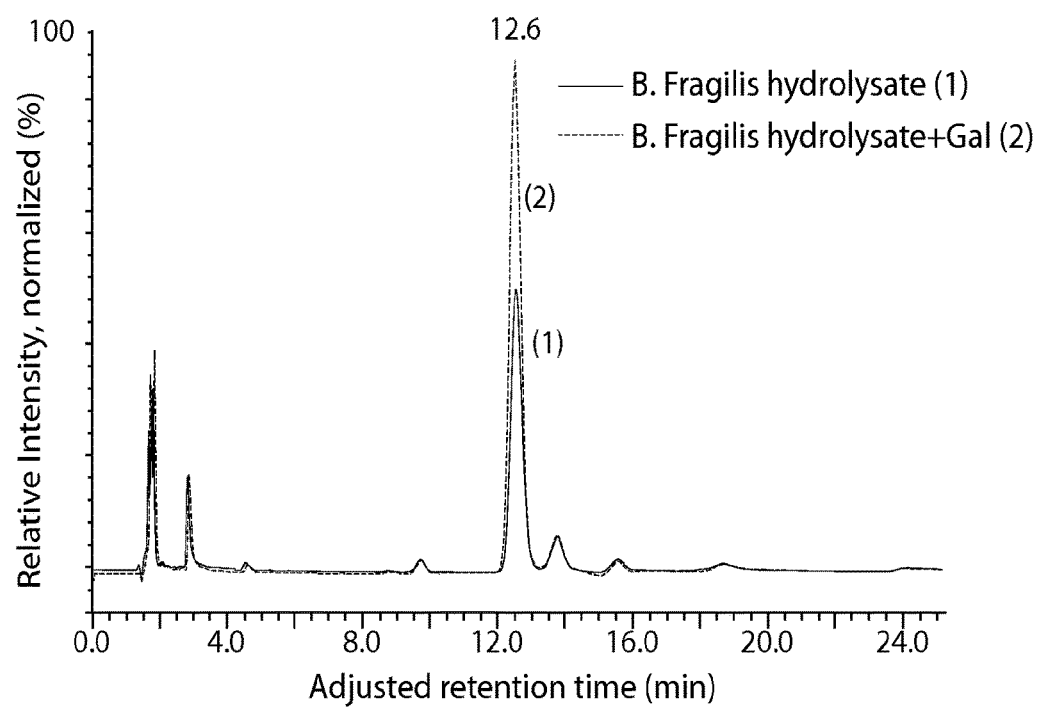
Figure 3D:
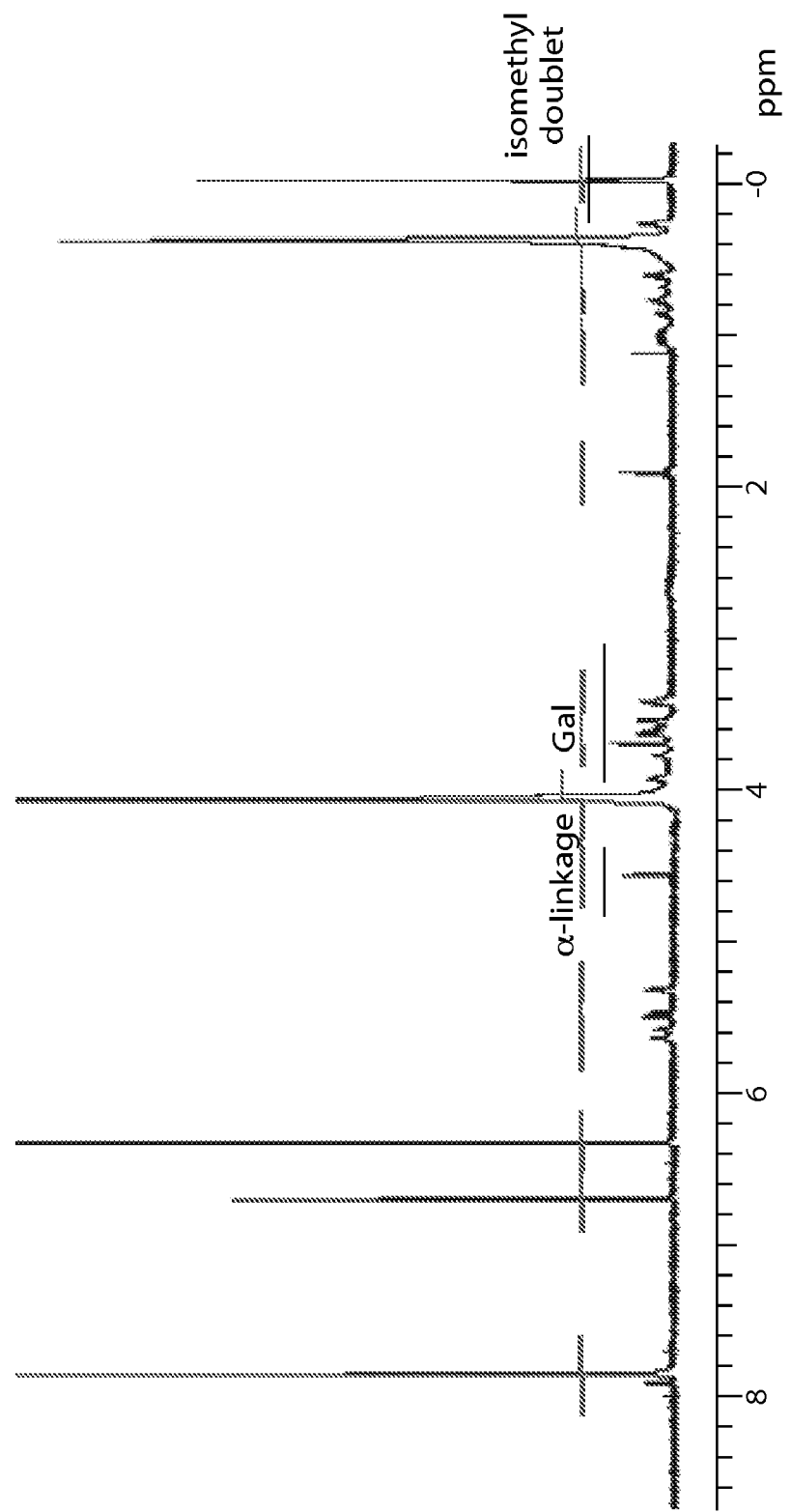
Figure 3E:
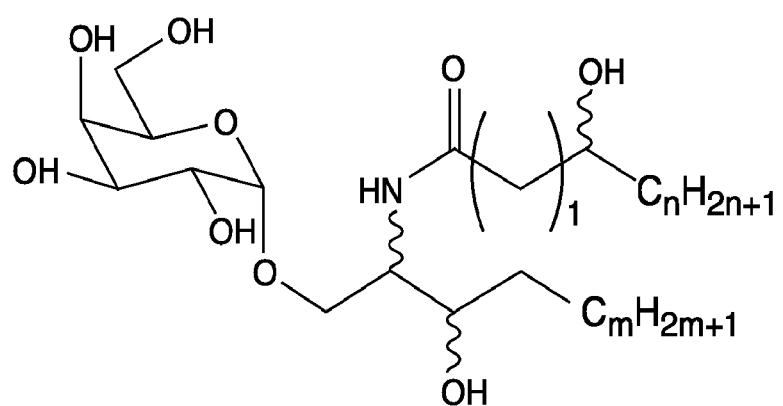
FIGS. 3E-G provide generic structures for the immunoinhibitory alpha-GC of the invention. In some embodiments, chain length distribution of the fatty acid is 3-hydroxy-15-methylhexanoic acid (3-OH-iso-C17, R=11). In some embodiments, the chain length of the sphingosine base is more broadly distributed from C16-C19. The most abundant species is C17 (where R'=10). Side chain groups may be present in the fatty acid and/or sphingosine base.
Figure 3F:
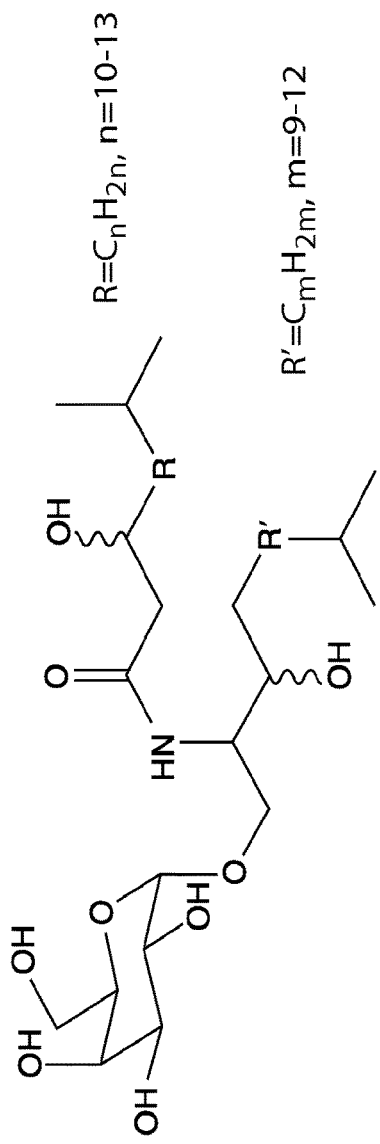
Figure 3F:
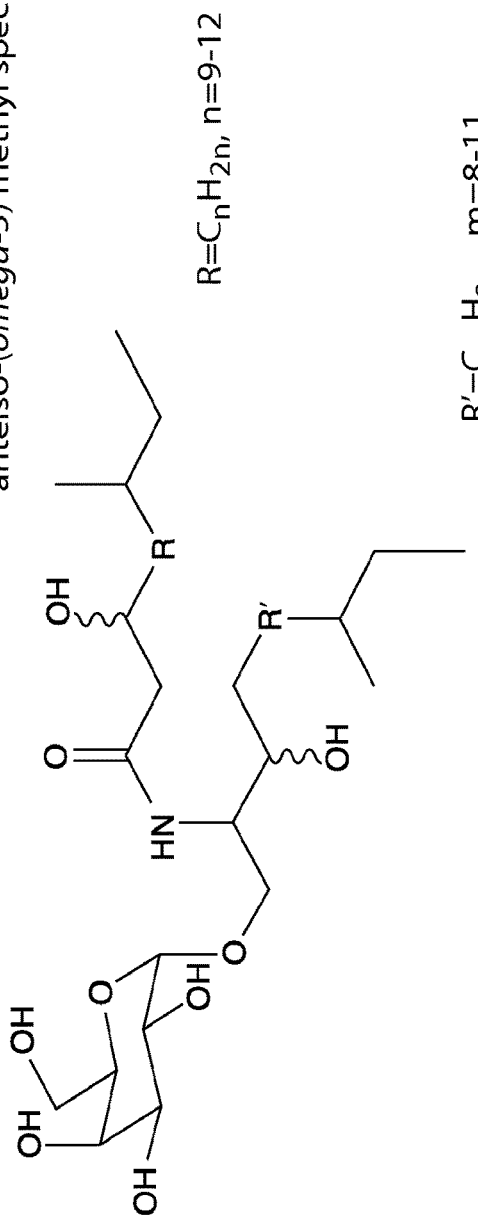
Figure 3G:
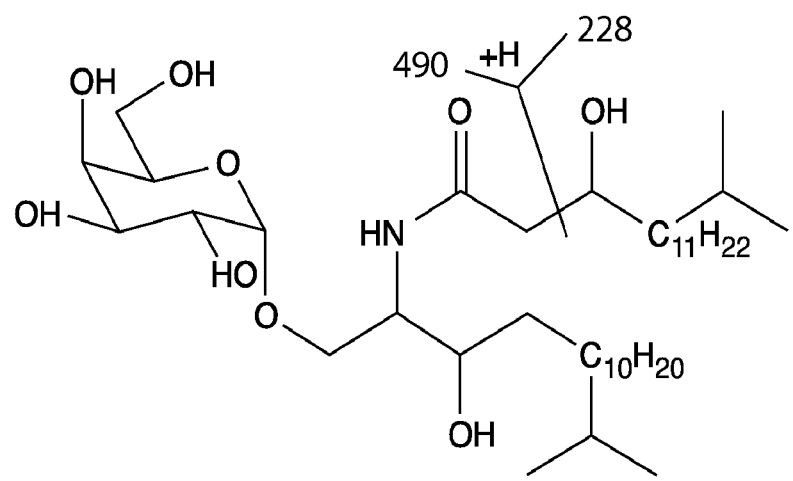

The fatty acid and sphingosine chains may be of the same length or of different lengths. These chains are typically less than 20 carbons (C20) in length, and more preferably are 15-19 carbons (C15-C19) in length, including 16-19 carbons in length. Some species will have at least one chain that is 17 carbons (C17) in length. Generic structures of the immunoinhibitory alpha-GC molecules of the invention are shown in FIGS. 3E and 3F. An alpha-GC species of the invention having a 17 carbon (C17) fatty acid chain and 17 carbon (C17) sphingosine chain is shown in FIG. 3G.

The fatty acid and sphingosine chains of the alpha-GC may be unbranched or branched. Branching may occur at one or more positions on the fatty acid and/or the sphingosine carbon chains. The branch may be of any length. In some instances, the branch point is at the penultimate carbon in the chain (referred to as the omega-2 or iso position). In some instances, the branch point is at the $3^{rd}$ last carbon in the chain (referred to as omega-3 or anteiso position). The alpha-GC species of FIG. 3G comprises terminal isomethyl groups on both the fatty acid and sphingosine chains. More generic structures are shown in FIGS. 3E and 3F.

The fatty acid and sphingosine chain may each independently comprise one or more hydroxyl groups. The position of the hydroxyl group may vary. In some instances, the hydroxyl group may be at the C2 position of the fatty acid chain. In some instances, the hydroxyl group may be at the C2 position of the sphingosine chain. In some instances, hydroxyl groups may be at both the C2 of the fatty acid and the C2 of the sphingosine. In some instances, the hydroxyl group may be at the C3 position of the fatty acid chain. In some instances, the hydroxyl group may be at the C3 position of the sphingosine chain. In some instances, hydroxyl groups may be at both the C3 of the fatty acid and the C3 of the sphingosine. An example of such a configuration is shown in FIG. 3G. In some instances, the hydroxyl group may be at the C4 position of the fatty acid chain. In some instances, the hydroxyl group may be at the C4 position of the sphingosine chain. In some instances, hydroxyl groups may be at both the C4 of the fatty acid and the C4 of the sphingosine. Any combination of hydroxyl substitutions at positions C1-C4 of the fatty acid and C1-C4 of the sphingosine chain are contemplated by the invention. More generic structures are shown in FIGS. 3E and 3F.

The alpha-GC may be provided as pure isomers or isomeric mixtures. Molecules that have the same molecular formula but differ in the nature or sequence of bonding of their atoms or the arrangement of their atoms in space are termed isomers. Isomers that differ in the arrangement of their atoms in space are termed stereoisomers. Stereoisomers that are not mirror images of one another are termed diastereomers and those that are non-superimposable mirror images of each other are termed enantiomers. When a molecule has an asymmetric center that, for example, is bonded to four different groups, then a pair of enantiomers is possible. An enantiomer can be characterized by the absolute configuration of its asymmetric center and can be described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing both enantiomers is called a "racemic mixture".

In the case of the alpha-GC of the invention, asymmetric centers are possible at least at carbons bonded to hydroxyl groups. At each such asymmetric carbon, the chirality may be an R or an S configuration. Any combination of chiralities at the various chiral carbons in the molecule are contemplated by the invention.

As an example, the C3 position in the fatty acid, if bonded to a hydroxyl, may be in the R configuration or the S configuration or alternatively the molecule as a whole may exist as a racemic mixture of molecules having either R or S configuration at that position. Similarly, the C3 position in the sphingosine chain, if bonded to a hydroxyl, may be in the R configuration or the S configuration or alternatively the molecule as a whole may exist as a racemic mixture of molecules having either R or S configuration at that position. The invention therefore contemplates every combination of chirality at these positions including R-R, R-S, S-S and S-R (i.e., chirality of the fatty acid C3 position and chirality of the sphingosine C3 position).

As another example, the C2 position in the fatty acid, if bonded to a hydroxyl, may be in the R configuration or the S configuration or alternatively the molecule as a whole may exist as a racemic mixture of molecules having either R or S configuration at that position. The C2 position in the sphingosine chain, if bonded to a hydroxyl, may be in the R configuration or the S configuration or alternatively the molecule as a whole may exist as a racemic mixture of molecules having either R or S configuration at that position. The invention therefore contemplates every combination of chirality at these positions including R-R, R-S, S-S and S-R (i.e., chirality of the fatty acid C2 position and chirality of the sphingosine C2 position).

As another example, the C4 position in the fatty acid, if bonded to a hydroxyl, may be in the R configuration or the S configuration or alternatively the molecule as a whole may exist as a racemic mixture of molecules having either R or S configuration at that position. The C4 position in the sphingosine chain, if bonded to a hydroxyl, may be in the R configuration or the S configuration or alternatively the molecule as a whole may exist as a racemic mixture of molecules having either R or S configuration at that position. The invention therefore contemplates every combination of chirality at these positions including R-R, R-S, S-S and S-R (i.e., chirality of the fatty acid C4 position and chirality of the sphingosine C4 position).

The term polymorphs refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a molecule can be prepared by crystallization under different conditions.

The GL-SL fraction may be used as an immunoinhibitory preparation in some aspects of the invention. This fraction may comprise one or more forms of immunoinhibitory alpha-GC and/or other forms of immunoinhibitory GL-SL that may or may not be characterized as galactose-bearing or ceramide-bearing.

The alpha-GC of the invention may be isolated. As used herein, the term isolated means partial or complete physical separation of the moiety of interest (e.g., the alpha-GC) from other moieties. In the case of alpha-GC that are obtained from a naturally occurring source, an isolated alpha-GC may be physically separated from the environment in which it naturally occurs (e.g., a *B. fragilis* cell or membrane). In the case of alpha-GC that are synthesized ex vivo, an isolated alpha-GC may be physically separated from the reaction mixture in which it was synthesized. Similar definitions apply to the immunoinhibitory GL-SL preparations of the invention.

The immunoinhibitory molecules of the invention, whether used individually or as a mixture of structurally different molecules, can be used alone or together with CD1d molecules. CD1d molecule is believed to bind to the immunoinhibitory molecules of the invention and facilitate presentation of the molecules to iNKT cells. Cells capable of presenting the molecules of the invention are therefore typically regarded as CD1d-positive antigen presenting cells. Examples of such cells include bone marrow derived dendritic cells. Certain aspects of the invention therefore contemplate use, including administration, of the immunoinhibitory alpha-GC and/or GL-SL when coupled (or bound or complexed) with isolated CD1d protein (i.e., CD1d protein that is not provided as an CD1d-bearing antigen presenting cell). In some instances, the CD1d protein is provided as a tetramer.

Without intending to be bound by any particular theory or underlying mechanism, the invention contemplates, inter alia, that the immunoinhibitory molecules provided herein are able to compete with immunostimulatory alpha-GC for binding to CD1 d and in this way reduce the efficacy of the immunostimulatory alpha-GC in the presence of iNKT cells.

As will be understood in view of this disclosure, one of ordinary skill in the art will be able to determine whether an alpha-GC or a GL-SL preparation is immunoinhibitory at least by virtue of its ability to antagonize the activity of immunostimulatory alpha-GC such as but not limited to KRN7000. Such assays can be performed in vitro or in vivo, with reference to the exemplary assays described in the Examples.

Uses—In Vitro and In Vivo

The invention contemplates in vitro and in vivo uses of the immunoinhibitory molecules and preparations provided herein. When used in vivo, the molecules and preparations may be formulated as pharmaceutical compositions (or preparations), intending that they are suitable for administration to a subject. A pharmaceutical composition need not be therapeutic or prophylactic however (i.e., it may not eradicate an existing condition or prevent a condition from ever occurring in a subject). Instead, it may be used to modulate an aberrant immune response such as an increased iNKT cell based immune response, and thereby optionally modulate symptoms resulting from the underlying iNKT cell based immune response. Such in vivo uses may be in subjects being treated for a particular condition characterized by increased iNKT cell numbers and/or iNKT cell activity with the intention of providing some therapeutic or prophylactic benefit. Alternatively, such the molecules and preparations may be used in vivo for research purposes, inter alia, typically in non-human subjects. The molecules and preparations may be used in vitro to modulate immune responses involving activated iNKT cells. Whether in vivo or in vitro, the molecules or preparations may be used in screening assays to identify iNKT cell stimulatory agents or inhibitory agents.

Whether in vivo or in vitro, the molecules or preparations may be used in a method that involves contacting the molecule(s) or preparation with an antigen presenting cell, and contacting the "loaded" antigen presenting cell with an iNKT cell(s). The antigen presenting cells typically will express CD1d on their surface. A "loaded" antigen presenting cell intends an antigen presenting cell that has an immunoinhibitory molecule of the invention bound to its CD1d and is therefore able to present such molecule to an iNKT cell. The contacting may occur in the presence of an agent that stimulates iNKT cells such as the alpha-GC KRN7000. The contacting may occur in the absence of such an immunostimulatory agent, and instead the iNKT cells may be activated iNKT cells. Such cells may have been activated in vitro prior to the contacting step or they may have been obtained from a subject having an increased iNKT cell based immune response. It is to be understood that these methods may be carried out in vivo or in vitro.

Conditions

The alpha-GC of the invention as well as fractions containing such alpha-GC may be used to treat conditions that are characterized by increased levels of iNKT cells and/or activity. An increased level of iNKT cells or activity is measured relative to a normal subject (or a normal population of subjects) not having an inflammatory condition and nor at increased (or elevated, intending above-normal) risk of developing such a condition (e.g., as may be the case if the condition is inherited). iNKT cells and/or activity may be measured in a blood sample or a biopsy such as a colonic (e.g., lamina propria) biopsy. Serum levels of proinflammatory cytokines, such as IFN-gamma, may be measured from the blood sample, for example. In some instances, persons having a family medical history or a personal medical history of a condition characterized by increased levels of iNKT cells and/or activity, such as for example colitis, arthritis, asthma, and the like, may be presumed to have or be at risk of developing the condition even if they are not experiencing symptoms at or near the time of treatment. In some instances, the subject may have an allergy or an allergic disorder. In some instances, activated iNKT cells are identified by the presence of CD1d tetramers, and may be detected and/or measured using for example flow cytometry or other immunostaining methods.

Such conditions include inflammatory conditions. Inflammatory conditions are conditions caused by, resulting from, or resulting in inflammation. An inflammatory condition may also refer to a dysregulated inflammatory reaction that causes an exaggerated response by macrophages, granulocytes, and/or T-lymphocytes leading to abnormal tissue damage and/or cell death. An inflammatory condition can be either an acute or chronic inflammatory condition and can result from infections or non-infectious causes. An inflammatory condition may be an autoimmune disease or it may be a non-autoimmune disease.

Inflammatory conditions include, without limitation, atherosclerosis, arteriosclerosis, polymyalgia rheumatica (PMR), gouty arthritis, degenerative arthritis, tendonitis, bursitis, psoriasis, cystic fibrosis, arthrosteitis, giant cell arteritis, polymyositis, dermatomyosis, pemphigus, pemphigoid, diabetes (e.g., Type I), myasthenia gravis, mixed connective tissue disease, sclerosing cholangitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fasciitis, and necrotizing enterocolitis.

Conditions characterized by increased levels of iNKT cells and/or activity may be autoimmune diseases. Autoimmune diseases are diseases arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications that decrease the immune response. Exemplary autoimmune diseases include, but are not limited to, multiple sclerosis, inflammatory bowel diseases such as ulcerative colitis, Crohn's disease, and ileitis, glomerulonephritis, Goodpasture's disease or syndrome, Graves' disease, necrotizing vasculitis, lymphadenitis, peri-arteritis nodosa, systemic lupus erythematosis, rheumatoid, arthritis, psoriatic arthritis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Reiter's syndrome, ankylosing spondylitis, Lyme arthritis, GuillainBarre syndrome, Hashimoto's thyroiditis, and cardiomyopathy.

The term "treat", "treated," "treating" or "treatment" is used herein to mean to relieve, reduce or alleviate at least one symptom of a condition characterized by increased iNKT cell numbers and/or activity in a subject. For example, treatment can be diminishment of one or several symptoms of such a condition or complete eradication of the condition. Within the meaning of the present invention, the term "treat" also denotes to arrest, delay the onset (i.e., the period prior to clinical manifestation of a condition) and/or reduce the risk of developing or worsening a condition. The term "protect" is used herein to mean prevent delay or treat, or all, as appropriate, development or continuance or aggravation of a condition in a subject.

A "subject" to which administration is contemplated includes, but is not limited to, humans and other non-human animals including, for example, companion animals such as dogs, cats, domesticated pigs, ferrets, hamsters, and the like; primates such as cynomolgus monkeys, rhesus monkeys, and the like; and agricultural animals such as cattle, pigs, horses, sheep, goats, birds (e.g., chickens, ducks, geese, and/or turkeys), and the like. In important embodiments, the subject is a human subject.

The subject may be of any age ranging from newborn to elderly. In some important embodiments, the subject is a pediatric subject such as a neonate, infant, child or adolescent. In such embodiments, the invention contemplates administering the active agents of the invention in order to render the subject resistant to conditions characterized by increased iNKT cell numbers or activity. As discussed herein, such conditions include but are not limited to asthma and autoimmune diseases such as but not limited to ulcerative colitis. Thus, the invention contemplates prophylactic treatment of a subject to prevent such conditions from manifesting. Accordingly, in some embodiments, the subject may be less than 10 years of age, less than 5 years of age, less than 1 year of age, less than 6 months of age, or less than 1 month of age. The invention further contemplates administration of older subjects such as adults. The subject may be a pregnant subject or a female subject of child-bearing age, either of which may optionally be at increased risk of developing a condition characterized by increased iNKT cell numbers and/or activity (e.g., an autoimmune disease, asthma, and the like). These latter embodiments are premised, at least in part, on the surprising finding that it was possible to impart resistance to offspring by administering alpha-GC to their mother during pregnancy. This finding, among others, suggested that iNKT cell numbers may be set early in life, thereby dictating whether a person is more likely or less likely to develop conditions characterized by increased iNKT cell numbers and/or activity.

The invention further contemplates that subjects may be treated once, twice or more times, over a period of time. This period of time may be days, weeks, months, or years. As an example, the agents may be administered daily or weekly in a subject experiencing symptoms associated with a condition characterized by increased iNKT cell numbers or activity, until such symptoms are reduced or eliminated. As another example, the agents may be administered one or more times in the early years of life of a subject and then may be administered again after several years, as a "boost" to the original administration. This latter administration schedule could be similar to that used in more traditional vaccination schemes.

Some embodiments of the invention involve treatment of subjects having asthma or treatment of subjects prior to the onset of asthma (e.g., children). A "subject having asthma" is a subject that has a disorder of the respiratory system characterized by inflammation, narrowing of the airways and increased reactivity of the airways to inhaled agents. Asthma is frequently, although not exclusively associated with atopic or allergic symptoms. An "initiator" as used herein refers to a composition or environmental condition which triggers asthma. Initiators include, but are not limited to, allergens, cold temperatures, exercise, viral infections, and the like.

Additional Active Agents

The invention contemplates the administration of alpha-GC with one or more additional active agents. The additional active agents include but are not limited to immunosuppressants or anti-inflammatory agents, asthma medicaments, allergy medicaments, and the like. The additional active agents may be blocking antibodies although they are not so limited.

Immunosuppressants or anti-inflammatory agents are agents that suppress or reduce an immune response. General classes of anti-inflammatories include steroids, non-steroid anti-inflammatory drugs (NSAIDS), as well as various classes listed herein.

Non-limiting examples of immunosuppressants or anti-inflammatory agents include without limitation Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

Anti-inflammatory agents typically prescribed for autoimmune diseases include mesalamine.

The additional active agent may be an asthma medicament, meaning a medicament that reduces the symptoms, inhibits the asthmatic reaction, or prevents the development of an asthmatic reaction. Various types of medicaments for the treatment of asthma are described in the Guidelines For The Diagnosis and Management of Asthma, Expert Panel Report 2, NIH Publication No. 97/4051, Jul. 19, 1997, the entire contents of which are incorporated herein by reference. Asthma medicaments include, but are not limited, PDE-4 inhibitors, Bronchodilator/beta-2 agonists, K+ channel openers, VLA-4 antagonists, Neurokin antagonists, TXA2 synthesis inhibitors, Xanthanines, Arachidonic acid antagonists, 5 lipoxygenase inhibitors, Thromboxin A2 receptor antagonists, Thromboxane A2 antagonists, Inhibitor of 5-lipox activation proteins, and Protease inhibitors.

Bronchodilator/beta-2 agonists are a class of compounds which cause bronchodilation or smooth muscle relaxation. Bronchodilator/beta-2 agonists include, but are not limited to, salmeterol, salbutamol, albuterol, terbutaline, D2522/formoterol, fenoterol, bitolterol, pirbuerol methylxanthines and orciprenaline Long-acting beta-2 agonists include, but are not limited to, salmeterol and albuterol. These compounds are usually used in combination with corticosteroids. Methylxanthines, including for instance theophylline, have been used for long-term control and prevention of symptoms. Short-acting beta-2 agonists include, but are not limited to, albuterol, bitolterol, pirbuterol, and terbutaline.

Allergy medicaments include, but are not limited to, anti-histamines, steroids, and prostaglandin inducers. Anti-histamines include, but are not limited to, loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, and HSR 609. Prostaglandin inducers include, but are not limited to, S-5751. The steroids include, but are not limited to, beclomethasone, fluticasone, tramcinolone, budesonide, corticosteroids and budesonide.

Corticosteroids include, but are not limited to, beclomethasome dipropionate, budesonide, flunisolide, fluticaosone, propionate, and triamcinoone acetonide. Systemic corticosteroids include, but are not limited to, methylprednisolone, prednisolone and prednisone.

Immunomodulators include, but are not limited to, the group consisting of anti-inflammatory agents, leukotriene antagonists, IL-4 muteins, soluble IL-4 receptors, immunosuppressants (such as Tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and, and Downregulators of IgE.

Leukotriene modifiers include, but are not limited to, zafirlukast tablets and zileuton tablets. Zileuton tablets function as 5-lipoxygenase inhibitors.

Other immunomodulators include neuropeptides such as substance P that have been shown to have immunomodulating properties. Substance P is a neuropeptide first identified in 1931 by Von Euler and Gaddum and see Chang et al. 1971. Nature (London) New Biol. 232:86-87 (1971).

Another class of compounds is the down-regulators of IgE. These compounds include peptides or other molecules with the ability to bind to the IgE receptor and thereby prevent binding of antigen-specific IgE. Another type of downregulator of IgE is a monoclonal antibody directed against the IgE receptor-binding region of the human IgE molecule. Thus, one type of downregulator of IgE is an anti-IgE antibody or antibody fragment. Anti-IgE is being developed by Genentech. One of skill in the art could prepare functionally active antibody fragments of binding peptides which have the same function. Other types of IgE downregulators are polypeptides capable of blocking the binding of the IgE antibody to the Fc receptors on the cell surfaces and displacing IgE from binding sites upon which IgE is already bound.

These types of asthma medications are sometimes classified as long-term control medications or quick-relief medications. Long-term control medications include compounds such as corticosteroids (also referred to as glucocorticoids), methylprednisolone, prednisolone, prednisone, chromolyn sodium, nedocromil, long-acting beta2-agonists, methylxanthines, and leukotriene modifiers. Quick relief medications are useful for providing quick relief of symptoms arising from allergic or asthmatic responses. Quick relief medications include short-acting beta2 agonists, anticholinergics and systemic corticosteroids. Anticholinergics include, but are not limited to, ipratrapoium bromide.

When two or more agents are administered to a subject, these can be administered simultaneously (e.g., where they are pre-mixed and administered together), substantially simultaneously (e.g., where they are administered one after another in the time it would take a medical practitioner to administer two agents to a subject), or sequentially with a period of time lapsing between the administrations. The two or more agents can also be administered by the same route or by a different route. For example, the agents may be all administered by inhalation. As another example, one agent may be administered by injection and another may be administered by inhalation.

Pharmaceutical Compositions

The agents may be used (e.g., administered) in pharmaceutically acceptable preparations (or pharmaceutically acceptable compositions), typically when combined with a pharmaceutically acceptable carrier. Such preparations may routinely contain pharmaceutically acceptable concentrations of salt, buffering agents, preservatives, compatible carriers, and may optionally comprise other (i.e., secondary) therapeutic agents, as discussed above.

A pharmaceutically acceptable carrier is a pharmaceutically acceptable material, composition or vehicle, such as a liquid or solid filler, diluent, excipient, solvent or encapsulating material, involved in carrying or transporting a prophylactically or therapeutically active agent. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

The agents, when it is desirable to deliver them systemically, may be formulated for parenteral administration by injection, including for example by bolus injection or continuous infusion. Formulations for injection may be presented in unit dosage form, e.g., in ampoules or in multi-dose containers, with or without an added preservative.

The compositions may take such forms as water-soluble suspensions, solutions or emulsions in oily or aqueous vehicles, and may contain formulatory agents such as suspending, stabilizing and/or dispersing agents. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase solubility. Alternatively, the agents may be in lyophilized or other powder or solid form for constitution with a suitable vehicle, e.g., sterile pyrogen-free water, before use.

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,675,189 and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be desirable. Long-term release, are used herein, means that the implant is constructed and arranged to delivery therapeutic levels of the active ingredient for at least 30 days, and preferably 60 days. Long-term sustained release implants are known to those of ordinary skill in the art and include some of the release systems described above.

Effective Amounts

The preparations of the invention are administered in effective amounts. An effective amount is that amount of an agent that alone stimulates the desired outcome. In some embodiments, the desired outcome is a decrease in the number and/or activity of iNKT cells (e.g., activated iNKT cells). In some embodiments, the desired outcome is a decrease or elimination of symptoms associated with a condition characterized by increased number and/or activity of iNKT cells.

The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a molecule or a preparation for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a molecule per unit dosage form.

In certain embodiments, the agents may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Administration Routes

The agents and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

In some embodiments, the alpha-GC are administered by any route that effects delivery to the lungs. Systemic administration routes such as intravenous bolus injection or continuous infusion are suitable. More direct routes such as intranasal administration, intratracheal administration (e.g., via intubation), and inhalation (e.g., via an aerosol through the mouth or nose) are also contemplated by the invention and in some instances may be more appropriate particularly where rapid action is necessary. As used herein, an aerosol is a suspension of liquid dispersed as small particles in a gas, and it includes a fine mist or a spray containing such particles. As used herein, aerosolization is the process of producing of an aerosol by transforming a liquid suspension into small particles or droplets. This may be done using an aerosol delivery system such as a pressurized pack or a nebulizer. Nebulizers include air-jet (i.e., pneumatic), ultrasonic, and vibrating-mesh nebulizers, for example with the use of a suitable propellant such as but not limited to dichlorodifluoromethane, trichlorofluoromethane, dichlorotetrafluoroethane, carbon dioxide or other suitable gas. In addition to nebulizers, other devices for pulmonary delivery include but are not limited to metered dose inhalers (MDIs) and dry powder inhalers (DPIs). Capsules and cartridges of for example gelatin for use in an inhaler or insufflator may be formulated containing lyophilized agents and a suitable powder base such as lactose or starch.

Kits

The invention also encompasses a packaged and labeled pharmaceutical product. This article of manufacture or kit includes the appropriate unit dosage form in an appropriate vessel or container such as a glass vial or plastic ampoule or other container that is hermetically sealed. Preferably, the article of manufacture or kit further comprises instructions on how to use including how to administer the pharmaceutical product. The instructions may further contain informational material that advises a medical practitioner, technician or subject on how to appropriately prevent or treat the disease or disorder in question. In other words, the article of manufacture includes instructions indicating or suggesting a dosing regimen for use including but not limited to actual doses, monitoring procedures, and other monitoring information.

In some embodiments, the unit dosage form should be suitable for pulmonary delivery for example by aerosol.

As with any pharmaceutical product, the packaging material and container are designed to protect the stability of the product during storage and shipment.

The kits may include agents in sterile aqueous suspensions that may be used directly or may be diluted with normal saline for intravenous injection or use in a nebulizer, or dilution or combination with surfactant for intratracheal administration. The kits may therefore also contain the diluent solution or agent, such as saline or surfactant. The kit may also include a pulmonary delivery device such as a nebulizer or disposable components therefore such as the mouthpiece, nosepiece, or mask.

EXAMPLES

The following Examples are meant for illustrative purposes, and are not meant to be exclusive or limiting.

The conventional iNKT-cell based immunotherapy has been aimed to expand iNKT cells, stimulate functional cytokine productions, especially IFN-gamma, and potentiate TH1 type responses. The discovery of alpha-GC-C17Cer facilitates treatment of iNKT cell mediated conditions by dampening the pro-inflammatory cytokine production and/or decreasing iNKT cell numbers in anatomic sites such as the colon and the lung. Such effects will be useful in the treatment of conditions such as autoimmune diseases in which iNKT cells are implicated, including without limitation ulcerative colitis, lupus and multiple sclerosis, as well as other inflammatory conditions such as asthma.

FIG. 1A illustrates the biosynthetic pathway through which complex sphingolipids are produced in bacteria such as B. fragilis. Indicated in the box is serine palmitoyltransferase (SPT), the first committed enzyme in sphingolipid biosynthesis. SPT produces 3-ketosphinganine from palmitoyl-CoA and serine (E values ≤E-44 by standard BLASTP search). SPT was genetically knocked-out in B. fragilis NCTC 9343 to generate bacterial mutants lacking sphingolipids in their membranes (BFΔSPT). The BFΔSPT mutant was complemented with a full copy of BF2461 in trans (referred to as "C-delta" herein). The BFΔSPT mutant was confirmed to produce no sphingolipids, whereas C-delta conferred the wild-type profile of sphingolipid generation.

Figure 1B:
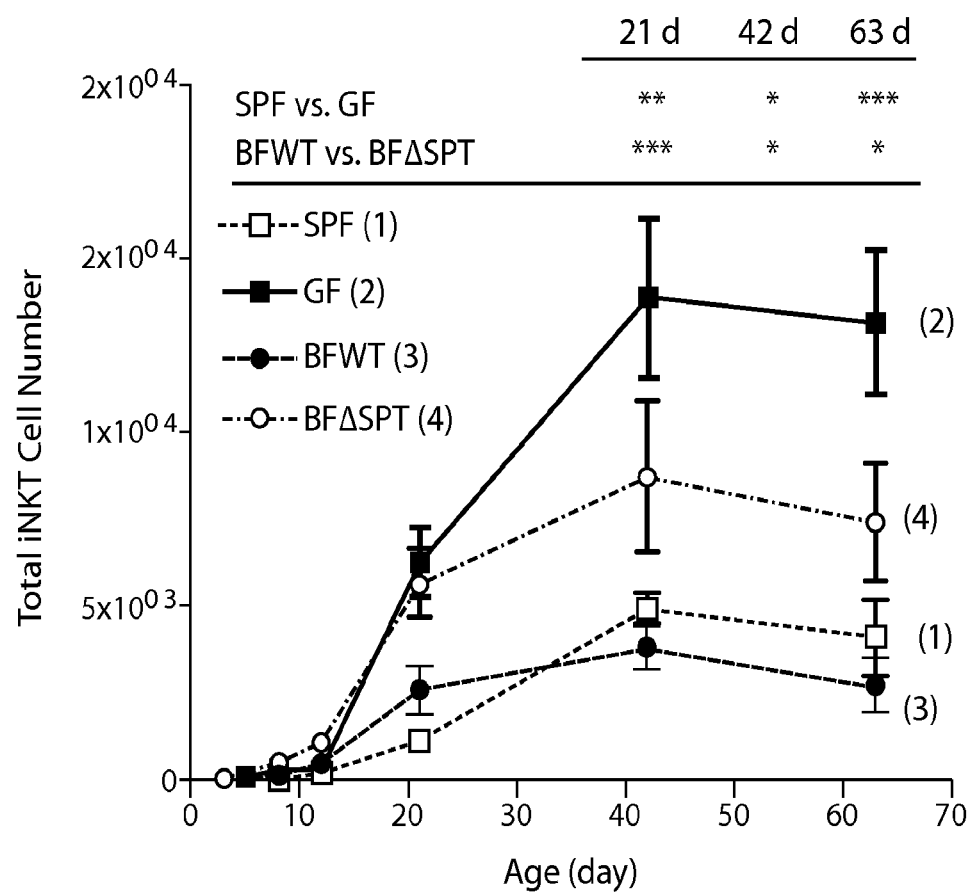
FIGS. 1B-C show that *B. fragilis* sphingolipids modulate colonic lamina propria (LP) iNKT cells in mice.
Figure 1C:
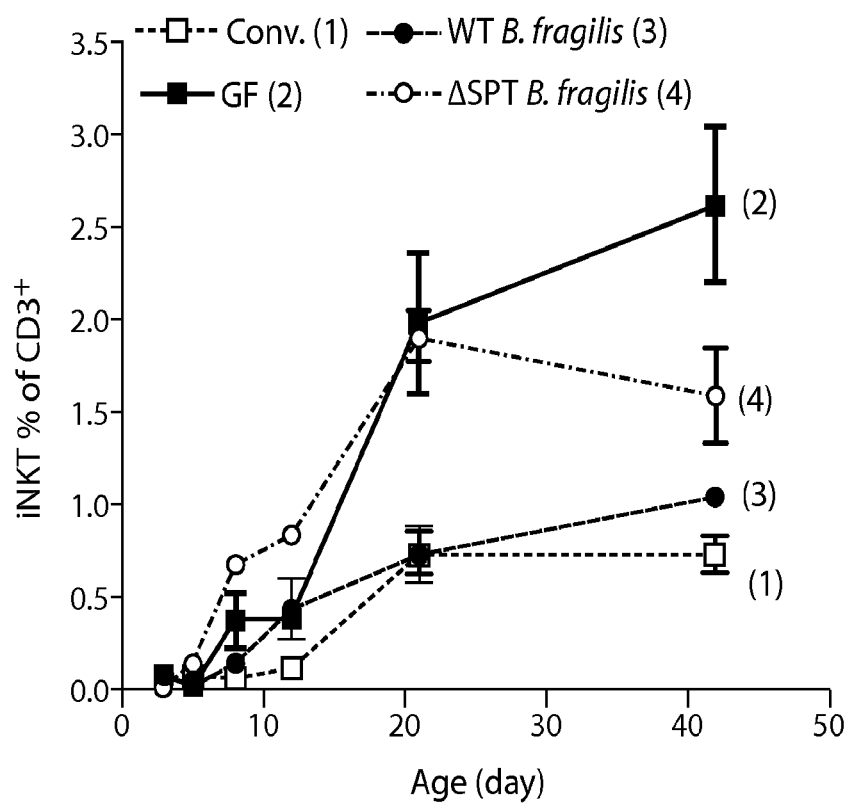

FIG. 1B shows the results of studies analyzing the dynamics of iNKT cell numbers in colonic LP. Germ-free mice were colonized with wild type (BFWT) or BFΔSPT (referred to herein as mutant or "mt") B. fragilis bacteria. These mice were then bred (BFWT×BFWT and BFΔSPT×BFΔSPT) to generate pups. Such pups were then sacrificed at various ages and their colonic iNKT cells were analyzed. "Cony" refers to mice colonized with conventional commensal microbiomes. "GF" refers to mice that are germ-free. At the time of sacrifice, LI LPL cells were harvested and purified. Live iNKT cells were detected by flow cytometry. iNKT cells were absent from the colon in all mice at birth and gradually increased in number until reaching a steady state at the age of 6 weeks. The Figure shows that LI LPL iNKT cell numbers increase after birth in all groups but were higher in GF and the delta-SPT mutant mono-colonized mice than in SPF and wild-type mono-colonized mice, a result suggesting that bacterial sphingolipids negatively regulate iNKT cell numbers in the colon. C-delta mono-associated mice had colonic iNKT cell numbers similar to those in BFWT mice. FIG. 1C is derived from the same data set as in FIG. 1B except that the data are represented as a percentage of CD3 positive cells.

The data show that mono-colonization by WT B. fragilis (BFWT) can change GF mice iNKT cell numbers to a level similar to SPF mice. However, the BFΔSPT (with one SPT gene knocked-out) mono-colonized mice can no longer rescue these cell numbers. These results demonstrate sphingolipids are important in modulating iNKT cells in LI LPLs.

Mono-colonization of GF mice with either BFWT or BFΔSPT bacteria did not change the iNKT levels in thymus, spleen, liver or lungs, or in the small intestine and Peyer's patches. These results indicate that B. fragilis sphingolipids exert effects on iNKT cells only in the colon, where this bacterium is most abundant.

Figure 1D:
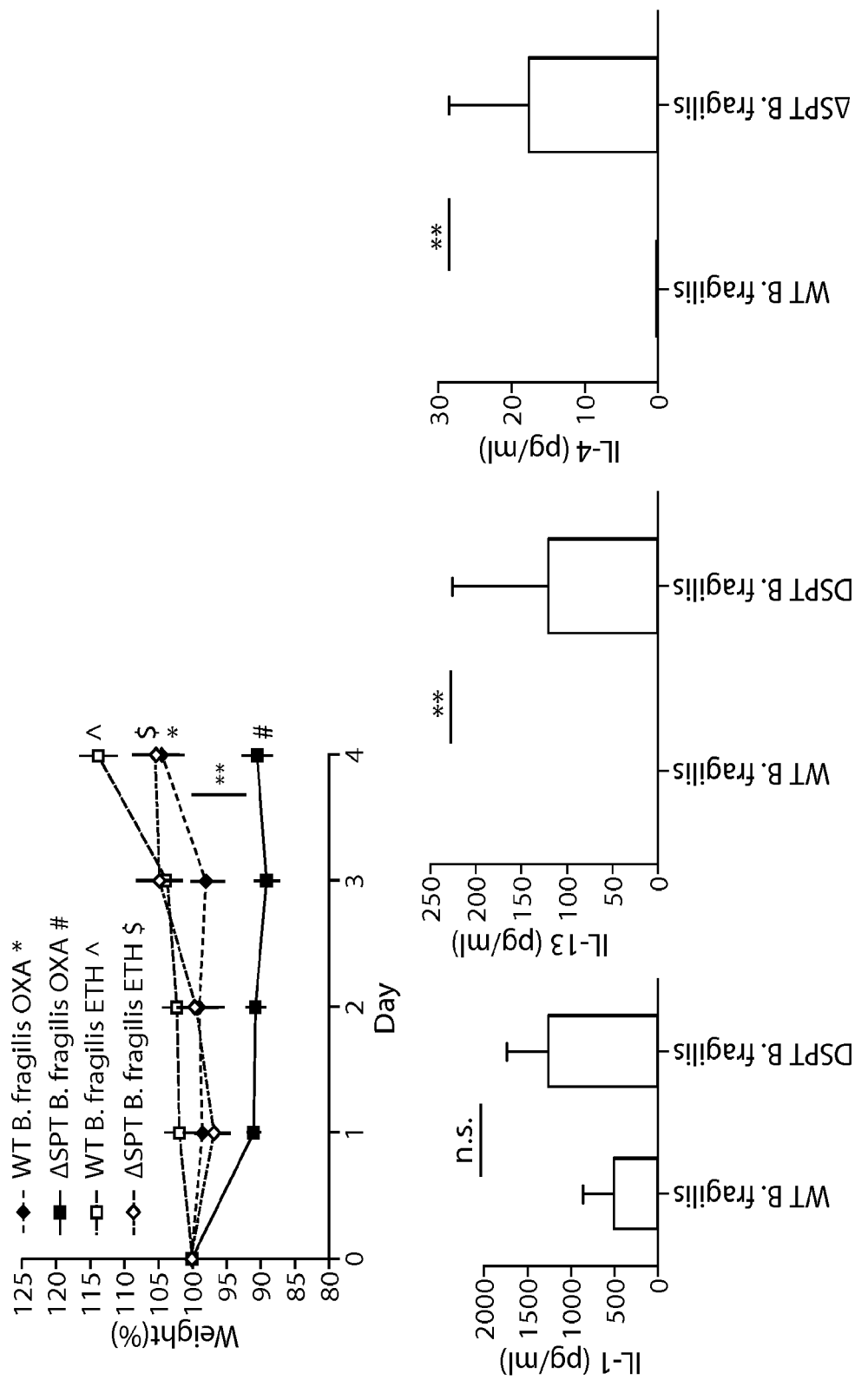
FIG. 1D shows weight loss and IL-1, IL-13 and IL-4 levels in BFΔSPT and BFWT mice upon oxazolone colitis challenge.

To investigate whether the observed difference between BFWT and BFΔSPT mice had biological significance, these mice were subjected to an oxazolone colitis challenge, in which intestinal inflammation characteristic of human ulcerative colitis is induced and is dependent on iNKT cell-produced interleukin 13 (IL-13). This experimental model of colitis is known in the art. 6-8 weeks old mice from each group were subjected to iNKT cell-mediated oxazolone colitis. The results are shown in FIG. 1D. Upon challenge, BFΔSPT mice had more severe weight loss (FIG. 1D) and inflammation, higher histopathology scores, and higher levels of IL-13, IL-4 and IL-1β release (FIG. 1D) than BFWT mice. Accordingly, BFWT mono-colonized mice were protected from oxazolone colitis while BFΔSPT mono-colonized mice were not, indicating that bacterial sphingolipids are important for protecting mice in an experimental model of oxazolone-induced colitis.

Figure 1E:
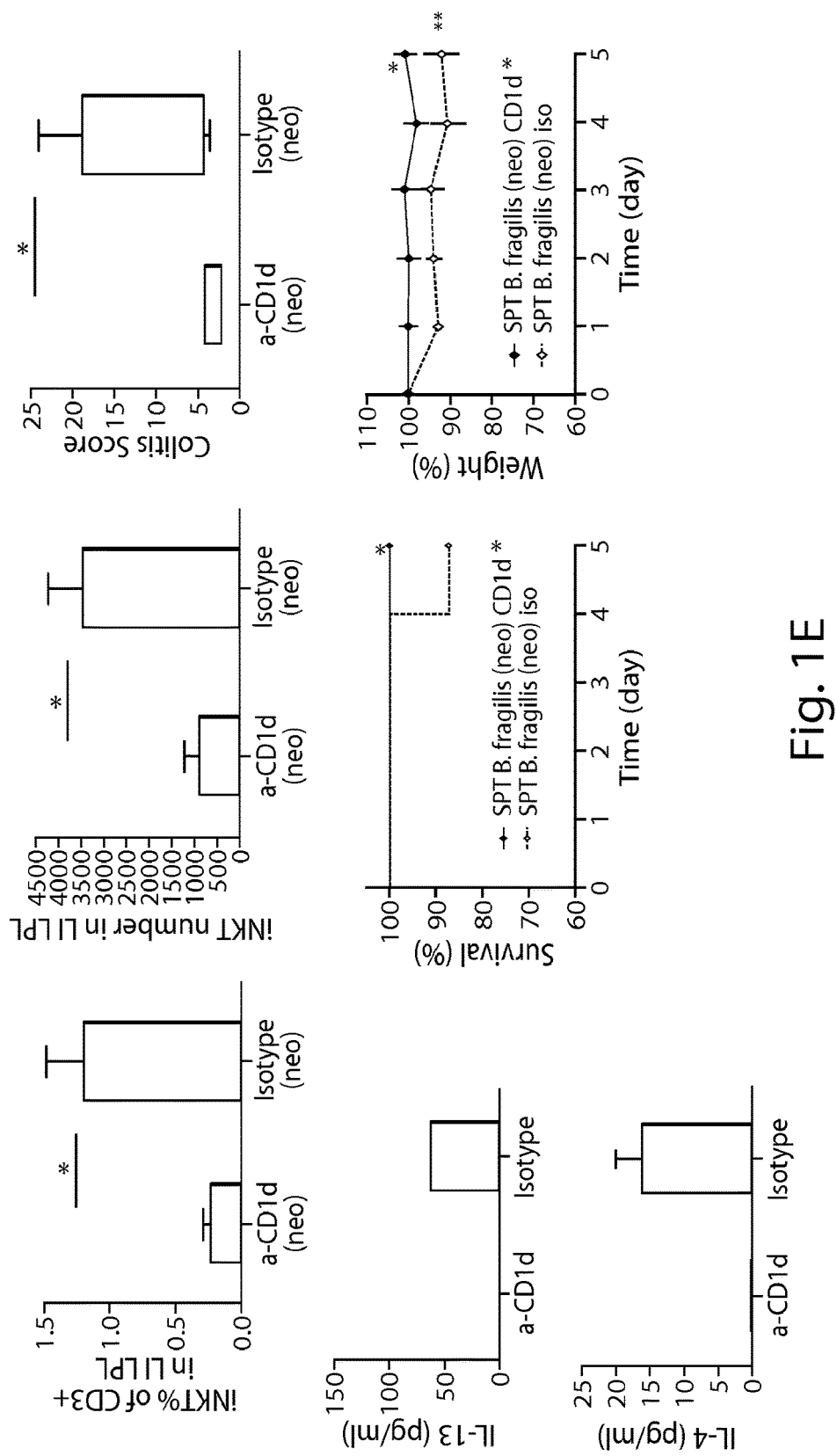
FIG. 1E shows that anti-CD1d antibody treated BFΔSPT mono-colonized mice (from birth) have decreased colonic LP iNKT cell numbers and a reduced oxazolone colitis phenotype.

To determine whether the oxazolone colitis phenotype observed in the BFΔSPT mono-colonized mice is iNKT cell mediated, these mice were treated with anti-CD1d monoclonal antibody (19G11). BFΔSPT mono-colonized mice were treated with anti-CD1d antibody or isotype control 3 times for the first 2 weeks after birth, followed by once a week for 4 weeks. At 6 weeks of age, mice from each group were subjected to iNKT cell-mediated oxazolone colitis. The results are shown in FIG. 1E. Anti-CD1d antibody treatment abrogated colitis while the isotype control did not. CD1d-iNKT mediated immune responses are therefore important for the colitis phenotype observed in the BFΔSPT mono-colonized mice.

Figure 1F:
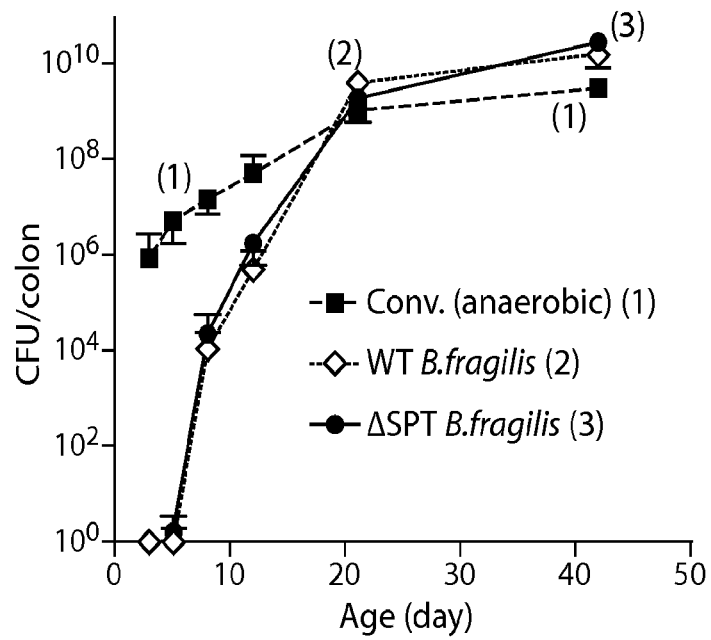
FIG. 1F shows quantification of bacterial CFU/colon in BFWT and BFΔSPT mono-colonized mice, and in SPF mice.
Figure 1F:
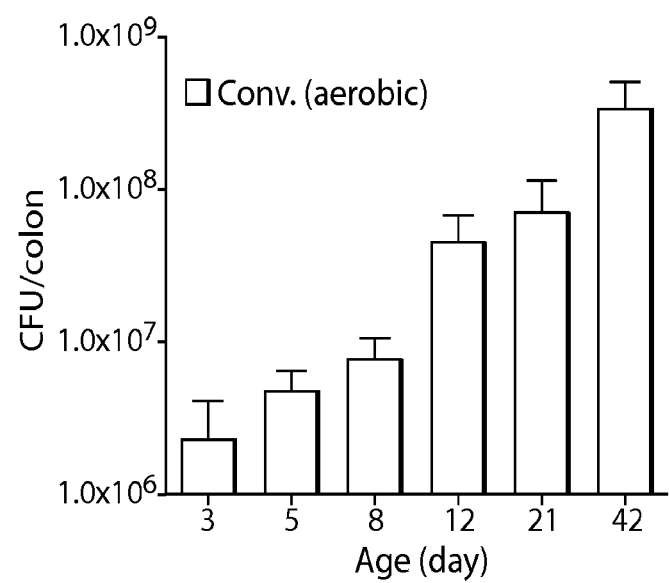

A number of possible causes for these observations were analyzed. FIG. 1F shows the results of experiments aimed to determine if the effect on colonic iNKT cell numbers was the result of differences in colonization by the BFWT and BFΔSPT (i.e., to rule out the possibility that the difference in the two mono-colonized mice is due to a difference of bacterial numbers in the colons of the two mice types). Stool samples from mice at designated ages were taken and measured for colony forming units (CFU). The results indicate that the two mono-colonized mice have identical colonization dynamics. Therefore, the WT and mutant mice are colonized by B. fragilis to the same extent and the numbers of bacteria in the colon cannot explain the observed iNKT cell phenotype.

Figure 1G:
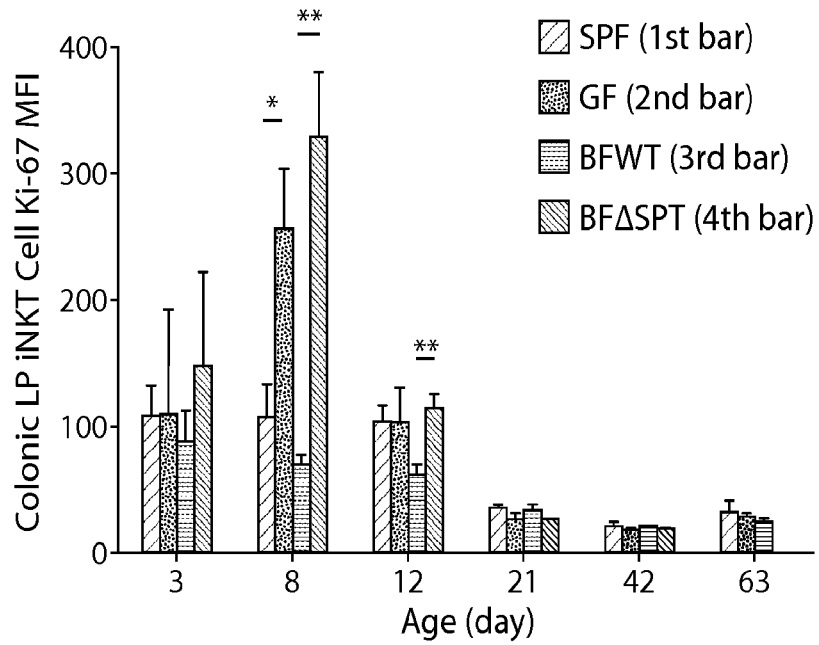
FIGS. 1G and 1H show that *B. fragilis* sphingolipids inhibit proliferation of colonic LP iNKT cells during neonatal development and restrict the accumulation of these cells in adult mice.
Figure 1H:
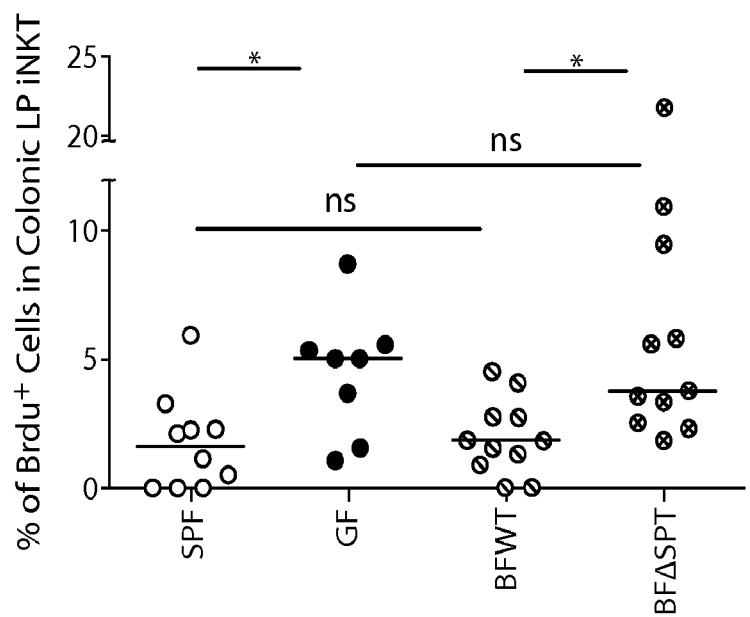

Further experiments indicated that neither differential CXCL16-mediated iNKT cell trafficking to the colon nor differential activation and apoptosis of colonic iNKT cells in BFWT and BFΔSPT mice were responsible for the observations. Another possible explanation for the observations is that the bacterial sphingolipids inhibit proliferation of iNKT cells. To test this hypothesis, expression of Ki-67 (a nuclear protein marker for cellular proliferation) was measured on iNKT cells in the colonic LP of mice from birth to 9 weeks of age. A significantly higher mean fluorescence intensity (MFI) for this protein was observed in GF and BFΔSPT mice than in SPF and BFWT mice during the neonatal period, particularly between days 5 and 12; proliferation was reduced to similar low levels in all mice after 21 days (FIG. 1G). To verify this observation, a bromodeoxyuridine (BrdU) method was used to measure DNA replication in colonic LP iNKT cells at 8 days of age in these mice. This confirmed that GF and BFΔSPT mice had a higher level of DNA replication in these cells than did SPF and BFWT mice (FIG. 1H). These studies showed that symbiotic bacterial sphingolipids can modulate the homeostasis of colonic iNKT cells by inhibiting cell proliferation during neonatal development.

On the basis of these findings, it was hypothesized that only when mice are exposed to symbiotic sphingolipids very early in life are their iNKT cell numbers restricted in adulthood. Two experiments were performed to test this hypothesis. In the first, BFWT bacteria were introduced into GF mothers during pregnancy. Ki-67 expression on pups' colonic LP iNKT cells was measured at 8 days of age, and total iNKT cell numbers were measured at 8 weeks. As expected, proliferation levels were lower and total cell numbers were similar in the pups born to mothers receiving BFWT bacteria [GF-WT(neo)] relative to values in BFWT mice. In the second experiment, we introduced BFWT bacteria into GF pups at 10-14 days of age [GF-WT(adu)], just after the cell proliferation window was closed. As expected, although GF-WT(adu) mice harbored numbers of BFWT bacteria equivalent to those in GF-WT(neo) mice, they had much higher colonic LP iNKT cell numbers at 8 weeks of age, comparable to numbers in GF mice. When further challenged with oxazolone, GF-WT(neo) mice responded similarly to BFWT mice, with a significant reduction in the severity of colitis phenotype and intestinal inflammation (as evidenced by weight-loss curves and colitis scores) from values in GF-WT(adu) mice. These studies established the importance of timing of exposure to sphingolipid-producing symbionts in maintaining host iNKT cell homeostasis and influencing disease susceptibility.

The chemical composition of *B. fragilis* sphingolipids was then analyzed to understand their function at the molecular level. Using thin-layer chromatography (TLC), high-performance liquid chromatography (HPLC), and mass spectrometry (MS), three types of sphingolipid fractions were found in this bacterium: ceramide sphingolipids, phosphorylethanolamine sphingolipids, and glycosphingolipids.

Figure 2A:
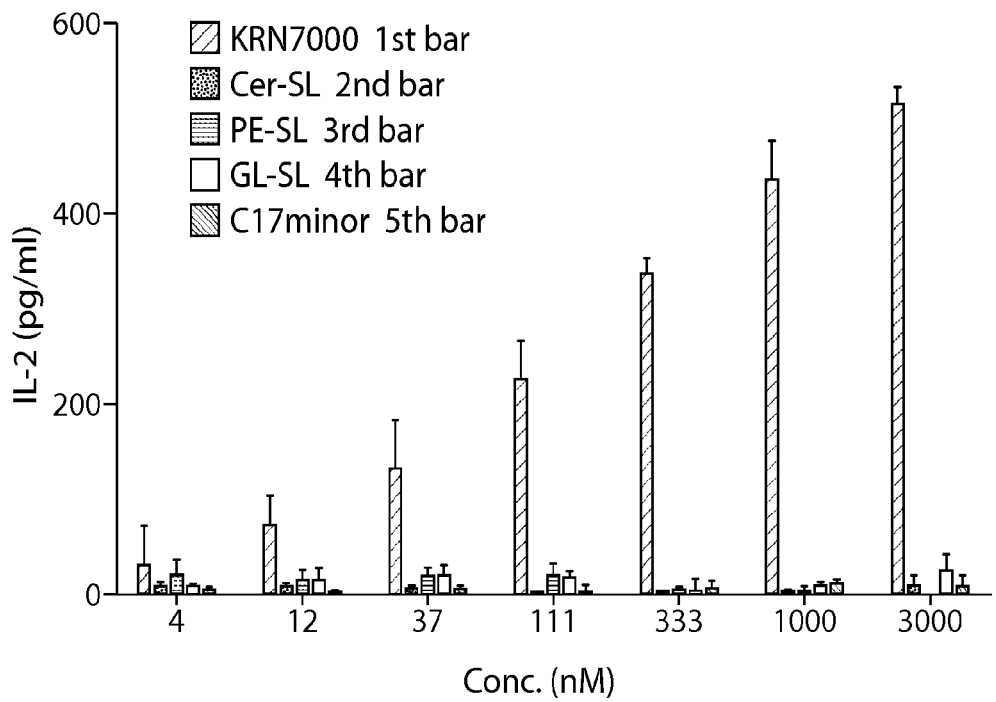
FIGS. 2A-B show that *B. fragilis* produces a sphingolipid molecule that acts as an iNKT cell antagonist.

Experiments were performed to determine whether fractions of *B. fragilis* sphingolipids are immunostimulatory (agonists) to iNKT cells. Lipid fractions were extracted from BF membranes, incubated with bone marrow dendritic cells (BMDCs) for 4 hours, and then co-incubated with iNKT hybridoma 24.7 for 24 hours. IL-2 was measured by ELISA as a readout of iNKT cell activation. The results are shown in FIG. 2A. KRN7000 refers to the known immunostimulatory alpha-GC. Cer-SL refers to the ceramide sphingolipid fraction. PE-SL refers to the phosphoethanolamine sphingolipid fraction. GL-SL refers to the glycosphingolipid fraction. C17 minor refers to alpha-GC having a C17 ceramide chain length. None of the *B. fragilis* sphingolipid fractions was found to activate the iNKT cell line. As expected, KRN7000 was stimulatory.

Figure 2B:
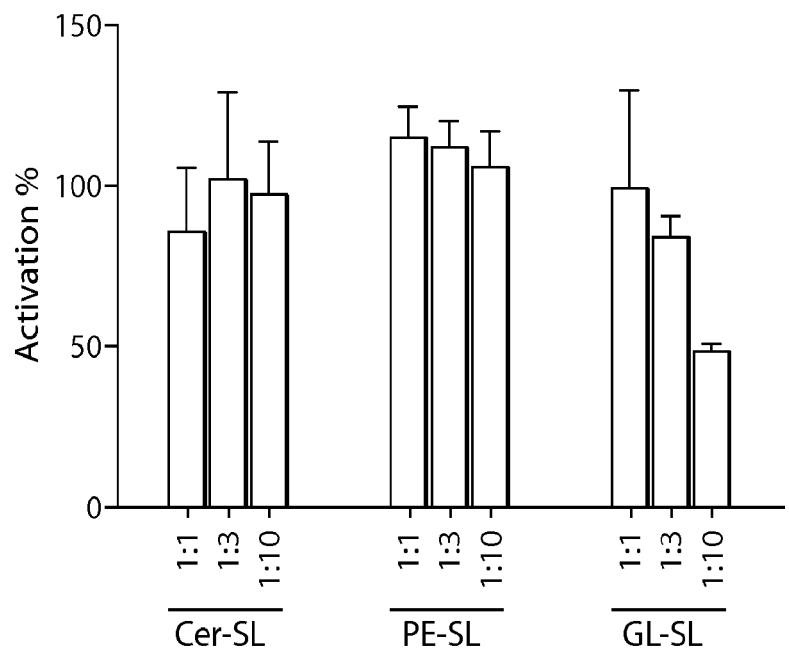

It was hypothesized that *B. fragilis* sphingolipids are likely to exert inhibitory effects by decreasing or inhibiting iNKT cell activation by agonists. To test this, BF sphingolipid fractions were incubated with BMDC in presence of 100 nM KRN7000 for 4 hours and then co-incubated with iNKT hybridoma 24.7 for 24 hours. IL-2 was measured by ELISA. FIG. 2B illustrates that GL-SL, but not Cer-SL or PE-SL, can antagonize the effects of the immunostimulatory alpha-GC KRN7000 in iNKT cells in vitro. This indicated that one or more molecules in the GL-SL fraction are antagonists of iNKT cell activation by KRN7000 in vitro. Such molecule(s) may also be capable of inhibition of other endogenous iNKT ligands in vivo.

To identify the specific molecule(s) antagonistic to iNKT activation, HPLC-MS was used to separate and characterize the GL-SL fraction. FIG. 3A shows the results of a LC-MS analysis that identified several chain-length variants of glycosphingolipids. The GL-SL fraction was composed of 5 subfractions with molecular weights ranging from m/z 688 to m/z 744 and total carbon numbers in ceramide structures ranging from 32 to 36.

The most abundant subtraction, m/z 716.7 (C 34), referred to as "peak 2" herein, was further purified and analyzed. The tandem mass spectrum of the glycosphingolipid at m/z of 716.7 (FIG. 3B) showed loss of single 18 Da mass, a finding characteristic of sphingoid backbone in the structure. In addition, the loss of mass with 162 Da and 180 Da suggested that a hexose head group was attached to the sphingoid chain.

$^1$H-NMR and $^1$H-1H-NMR (COSY) were used to characterize the structure of the monosaccharide head group and its glycosidic linkage. NMR analysis revealed a galactose residue linked alpha-glycosidically to the sphingoid backbone. Purified and hydrolyzed glycosphingolipid was analyzed by Dionex HPAEC. The major peak from the hydrolysate was spiked with a galactose standard. The results provided in FIG. 3C show that the sugar conjugated to *B. fragilis* glycosphingolipid is a galactose. Proton 1D NMR of lipid showed many characteristic chemical shifts, indicating the alpha-linkage of galactose and isomethyl terminal branching. These results are shown in FIG. 3D.

These findings confirm the structure of the immunoinhibitory *B. fragilis* glycosphingolipid as an alpha-galactosyl ceramide. This alpha-galactosylceramide, which shares key features with known iNKT cell agonists (e.g., KRN7000 and GSLs produced by *Sphingomonas*), is referred to as alpha-GC-C17 and alpha-GC-Bf717 interchangeably; a proposed generic structure is shown in FIG. 3E. Additional structures are provided in FIGS. 3F and 3G.

Further studies confirmed that alpha-GC-Bf717 was detectable only in fecal samples from BFWT mice and not in samples from BFΔSPT mice. The estimated yield of alpha-GC-Bf717 was about 1 ng per gram of fecal pellet. To confirm that alpha-GC-Bf717 had antagonistic activity, co-cultures similar to those described above for bulk GL-SL fractions were performed. In co-cultures of BMDCs and iNKT cell hybridoma 24.7, alpha-GC-Bf717 did not activate iNKT cells. This observation was confirmed when MODE-K cells were used as CD1d-expressing antigen-presenting cells and were co-cultured with iNKT cell hybridoma DN32. Alpha-GC-Bf717 also did not activate non-invariant NKT cell line 14S6.

Figure 4A:
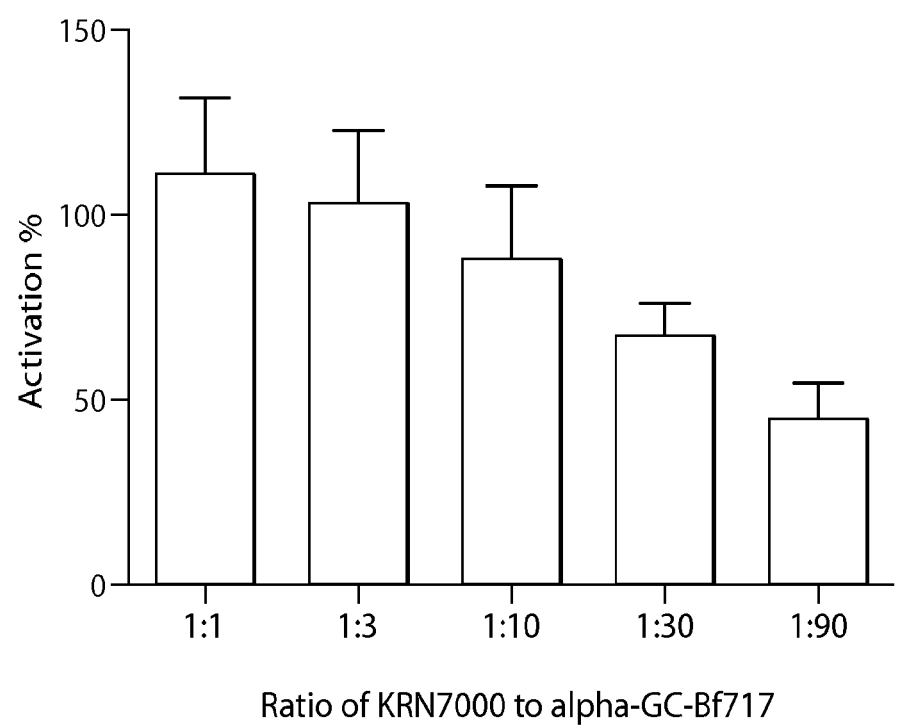
FIG. 4A shows antagonism of GL-SL peak 2 in the presence of KRN7000 (100 nM) in vitro.

Alpha-GC-Bf717 did however antagonize the effects of KRN7000 (100 nM) in vitro. This was shown by incubating different LC-MS purified GL-SL molecules with BMDC in presence of 100 nM KRN7000 for 4 hours and then co-incubating with iNKT hybridoma 24.7 for 24 hours. IL-2 was measured by ELISA. FIG. 4A shows that at least a portion of the antagonizing activity can be physically located in the alpha-GC-Bf717 fraction from GL-SL (i.e., peak 2). The activity was dose-dependent. (The ratios indicate the amount of KRN7000 to the amount of peak 2.)

It is likely that peak 2 contains a single molecule, potentially in an isomeric mixture, that is inhibitory to iNKT cell activation in vitro. When compared to the activity for the crude GL-SL preparation however it is apparent that the GL-SL preparation comprises inhibitory activity in addition to that of peak 2. Analysis of other LC-MS subfractions of the GL-SL fraction indicated that immunoinhibitory activity may be present in these also, albeit to different degrees.

Figure 4B:
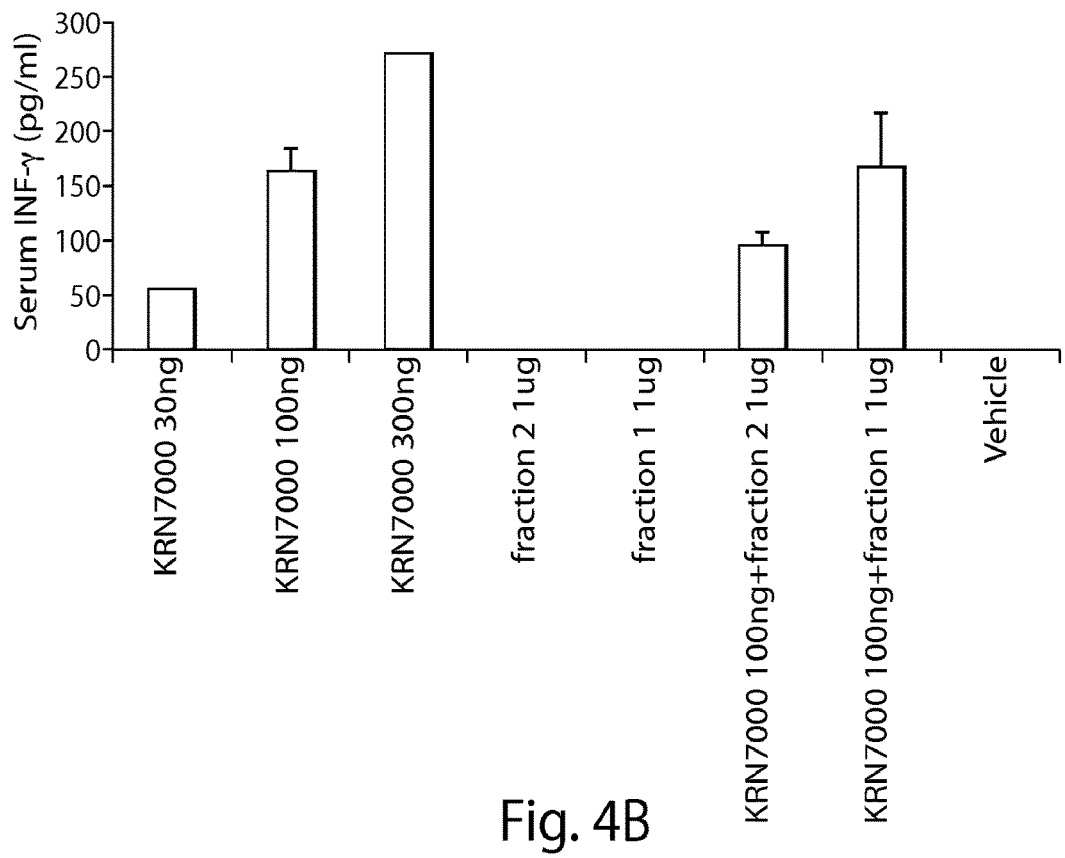
FIG. 4B shows iNKT cell antagonism by GL-SL peak 2 in the presence of KRN7000 in vivo using IFN-gamma as the readout after GL-SL peak 2 i.p. injection to SPF mice.

FIG. 4B shows that the antagonist effects of peak 2 are also apparent in vivo. iNKT cytokine (IFN-gamma) production in vivo was reduced in the presence of peak 2. Peak 2

(1 microgram) was injected i.p. into mice 1 hour before the injection of 100 ng KRN7000. Serum was collected after 4 hours and IFN-gamma was measured by ELISA. Fraction 1, in contrast, was not antagonistic. Peak 2 also significantly reduced the production of IL-4 in serum from the levels measured with KRN7000 alone. A purified *B. fragilis* control sphingolipid used at the same dose had no effect. In this experiment, the production of these cytokines through KRN7000 stimulation was mediated by iNKT cells and dependent on CD1d expression: no IFN-γ or IL-4 was produced in CD1d-knockout mice in any group. These results demonstrate that the antagonism of GL-SL peak 2 observed in vitro is also apparent in vivo. It is likely that this inhibition leads to decreased iNKT cell numbers.

To determine whether this inhibition takes place at the interface between the CD1d molecule and the iNKT cell receptor, a lipid-loading experiment was performed, using PE (phycoerythrin)-stained CD1d empty tetramers and iNKT cell hybridoma 24.7. Only lipid-loaded CD1d tetramers bind to the iNKT cell surface receptor, and the complex can be detected by flow cytometry. Neither the three lipid fractions nor αGC-Bf717 alone could be loaded onto the tetramers and bound to iNKT cells. This experiment suggests that inhibition of iNKT cell activation by αGC-Bf717 occurs at the molecular interface between CD1d and the iNKT cell receptor. We speculate that, because of structural similarity, αGC-Bf717 can compete with iNKT cell agonists (e.g., KRN7000) for the limited space in CD1d grooves.

Figure 4C:
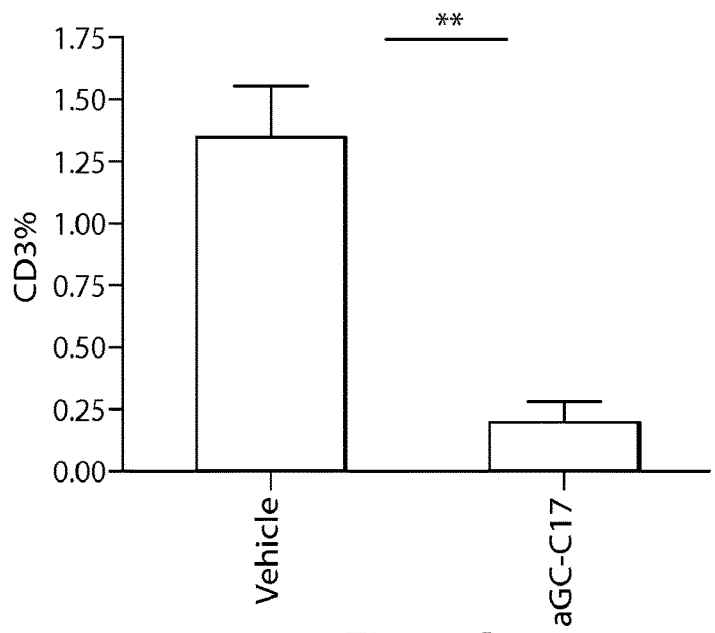
FIG. 4C shows that GL-SL peak 2 when administered i.p. to BFΔSPT mono-colonized mice decreases colonic LP iNKT cell numbers.
Figure 4D:
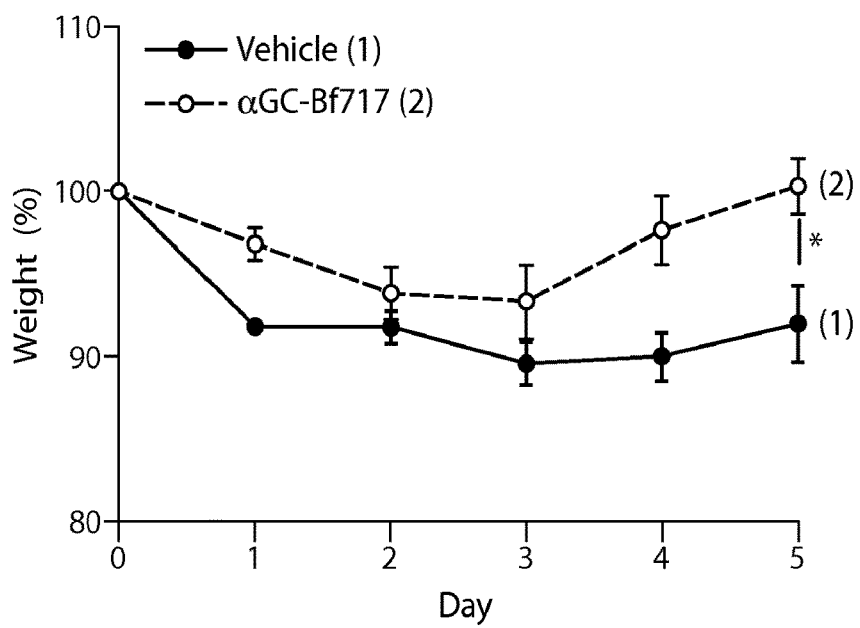
FIGS. 4D-E show that alpha-GC-Bf717 treatment of BFΔSPT mice provides protection from colitis. Alpha-GC-Bf717-treated mice were protected against oxazolone challenge, with less weight loss (D) and lower cumulative histopathology scores (E).
Figure 4E:
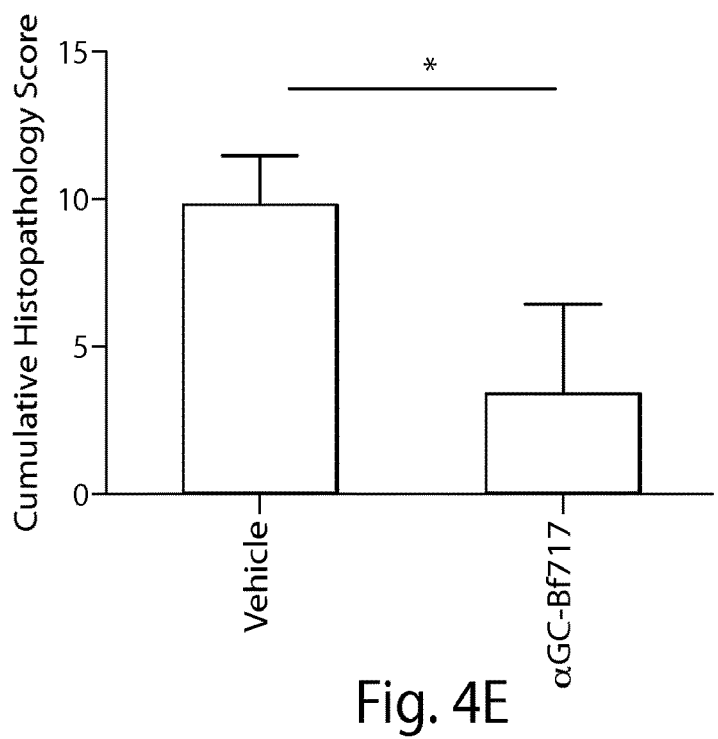

In vivo activation of iNKT cells is driven mostly by endogenous self-antigens whose identities are unclear. Our studies with KRN7000 suggested that αGC-Bf717 might inhibit in vivo activation and expansion of iNKT cells by endogenous lipids during the neonatal period. FIG. 4C shows the results of experiments designed to test if injection of peak 2 to BFΔSPT mono-colonized mice can rescue the iNKT phenotype in LI LPLs. 100-150 ng of fraction was i.p. injected to newborn mice at day 1, 3, 5 and 7. At 6 weeks, mice were harvested for iNKT cell measurement in LI LPLs. The results show that GL-SL peak 2 can decrease iNKT cell number in LI LPLs upon i.p. injection. When challenged with oxazolone, peak 2 treated mice lost less weight and had lower histopathology scores than did solvent-treated mice (FIGS. 4D and 4E). It is therefore a candidate therapeutic agent to interfere with iNKT number and function in relevant human diseases.

Discussion

Although in utero development is in a sterile environment, mammals commence a lifelong relationship with microbes at birth. Symbionts thus have the opportunity to affect host physiology from an early age, when many host functions are actively evolving. The results provided herein revealed an unexpected mechanism for the attainment of the host's immune balance: symbionts negatively regulate a crucial immune cell type, the iNKT cell, and prevent its excessive activation during disease challenge. This modulation is mediated by glycosphingolipids produced by the bacterial symbionts, which effectively blend into the host lipid antigen pool and inhibit iNKT cell activation and expansion caused by endogenous agonists during neonatal development. By modulating homeostasis of host lipid environments, symbionts help to maintain proper iNKT cell numbers and functions.

In addition, although both are α-glycosphingolipids, αGC-Bf717 is diametrically opposite—in terms of function—to the GSLs produced by pathobiont *Sphingomonas* species. This observation probably reflects fine structural differences between these molecules and thus their dissimilar interactions with CD1d and iNKT surface receptor. More importantly, the opposite phenotypes of αGC-Bf717 and GSLs reflect their profoundly different relationships to the host and highlight a fundamental difference between symbiosis and pathogenesis.

The identification herein of a bacterial sphingolipid that regulates iNKT cell homeostasis further blurs the conventional distinction between self and non-self in terms of immune recognition. The experimental data provided herein suggest that, during development, the host is profoundly dependent on αGC-Bf717 and similar molecules for iNKT cell homeostasis. Remarkably, the data showed that an absence of αGC-Bf717 and similar molecules in young GF and BFΔSPT mice had a lasting impact on the animals' iNKT cell homeostasis and caused an irreversible increase in their colitis susceptibility. The results highlight the importance of sphingolipid-producing symbionts as a vital component of the colonic microflora in early life. Although αGC-Bf717 is not encoded in the eukaryotic genome, the invention contemplates this molecule as a prototype for self-antagonist for iNKT cells.

It is unexpected to discover that a single molecule functions on behalf of the whole intestinal microbiota in regulating colonic iNKT cell homeostasis. Also notable is that αGC-Bf717 presence is important in a specific developmental time window. These limited examples strongly indicate that microbes modulate host immune functions with profound and diverse effects. In addition, with its unusual antagonistic properties, αGC-Bf717 may offer promise as a novel therapeutic intervention targeting the deleterious impact of iNKT cells in many human disorders.

REFERENCES

1 Bäckhed, F., Ley, R., Sonnenburg, J., Peterson, D. & Gordon, J. Host-bacterial mutualism in the human intestine. Science (New York, N.Y.) 307, 1915-1920, doi: 10.1126/science.1104816 (2005).
2 Chow, J., Lee, S., Shen, Y., Khosravi, A. & Mazmanian, S. Host-bacterial symbiosis in health and disease. Advances in immunology 107, 243-274, doi:10.1016/B978-0-12-381300-8.00008-3 (2010).
3 Honda, K. & Littman, D. The microbiome in infectious disease and inflammation. Annual review of immunology 30, 759-795, doi:10.1146/annurev-immunol-020711-074937 (2012).
4 Mazmanian, S., Liu, C., Tzianabos, A. & Kasper, D. An immunomodulatory molecule of symbiotic bacteria directs maturation of the host immune system. Cell 122, 107-118, doi:10.1016/j.cell.2005.05.007 (2005).
5 Mazmanian, S., Round, J. & Kasper, D. A microbial symbiosis factor prevents intestinal inflammatory disease. Nature 453, 620-625, doi:10.1038/nature07008 (2008).
6 Kato, M., Muto, Y., Tanaka-Bandoh, K., Watanabe, K. & Ueno, K. Sphingolipid composition in *Bacteroides* species. Anaerobe 1, 135-139 (1995).
7 Ingar, O. & Erik, J. Sphingolipids in Bacteria and Fungi. Anaerobe 7, doi:10.1006/anae.2001.0376 (2001).
8 Kinjo, Y. et al. Recognition of bacterial glycosphingolipids by natural killer T cells. Nature 434, 520-525, doi: 10.1038/nature03407 (2005).
9 Mattner, J. et al. Exogenous and endogenous glycolipid antigens activate NKT cells during microbial infections. Nature 434, 525-529 (2005).
10 Cohen, N., Garg, S. & Brenner, M. Antigen Presentation by CD1 Lipids, T Cells, and NKT Cells in Microbial Immunity. Advances in immunology 102, 1-94, doi: 10.1016/S0065-2776(09)01201-2 (2009).
11 Kronenberg, M. Toward an understanding of NKT cell biology:progress and paradoxes. Annu. Rev. Immunol. 26, 877-900 (2005).
12 Matsuda, J., Mallevaey, T., Scott-Browne, J. & Gapin, L. CD1d-restricted iNKT cells, the 'Swiss-Army knife' of the immune system. Current opinion in immunology 20, 358-368, doi:10.1016/j.coi.2008.03.018 (2008).
13 Olszak, T. et al. Microbial exposure during early life has persistent effects on natural killer T cell function. Science (New York, N.Y.) 336, 489-493, doi:10.1126/science.1219328 (2012).
14 Altschul, S., J C Wootton, E M Gertz, R Agarwala, A Morgulis, A A Schaffer, Y K Yu. Protein database searches using compositionally adjusted substitution matrices. FEBS J. 272, 5101-5109 (2005).
15 Lowther, J., Naismith, J., Dunn, T. & Campopiano, D. Structural, mechanistic and regulatory studies of serine palmitoyltransferase. Biochemical Society transactions 40, 547-554, doi:10.1042/BST20110769 (2012).
16 An, D., Na, C., Bielawski, J., Hannun, Y. & Kasper, D. Membrane sphingolipids as essential molecular signals for *Bacteroides* survival in the intestine. Proceedings of the National Academy of Sciences of the United States of America 108 Suppl 1, 4666-4671, doi:10.1073/pnas.1001501107 (2011).
17 Heller, F., Fuss, I., Nieuwenhuis, E., Blumberg, R. & Strober, W. Oxazolone colitis, a Th2 colitis model resembling ulcerative colitis, is mediated by IL-13-producing NK-T cells. Immunity 17, 629-638, doi:10.1016/S1074-7613(02)00453-3 (2002).
18 Schiechl, G. et al. Tumor development in murine ulcerative colitis depends on MyD88 signaling of colonic F4/80+CD11b(high)Gr1(low) macrophages. The Journal of clinical investigation 121, 1692-1708, doi:10.1172/JCI42540 (2011).
19 Fuss, I. et al. Nonclassical CD1d-restricted NK T cells that produce IL-13 characterize an atypical Th2 response in ulcerative colitis. The Journal of clinical investigation 113, 1490-1497, doi:10.1172/jci19836 (2004).
20 Wingender, G. et al. Intestinal microbes affect phenotypes and functions of invariant natural killer T cells in mice. Gastroenterology 143, 418-428, doi:10.1053/j.gastro.2012.04.017 (2012).
21 Rossjohn, J., Pellicci, D., Patel, O., Gapin, L. & Godfrey, D. Recognition of CD1d-restricted antigens by natural killer T cells. Nature reviews Immunology 12, 845-857, doi:10.1038/nri3328 (2012).
22 Strachan, D. P. Hay fever, hygiene, and household size. BMJ 299, doi:10.1136/bmj.299.6710.1259 (1989).
23 Wills-Karp, M., Santeliz, J. & Karp, C. The germless theory of allergic disease: revisiting the hygiene hypothesis. Nat Rev Immunol (2001).
24 Isolauri, E. K., Marko; Rautava, Samuli; Salminen, Seppo; Laitinen, Kirsi. Obesity—extending the hygiene hypothesis. Nestle Nutrition workshop series. Paediatric programme 64, 75-85 (2009).
25 Matangkasombut, P., Pichavant, M., Dekruyff, R. & Umetsu, D. Natural killer T cells and the regulation of asthma. Mucosal immunology 2, 383-392, doi:10.1038/mi.2009.96 (2009).
26 Peternel, S. & Kastelan, M. Immunopathogenesis of psoriasis: focus on natural killer T cells. Journal of the European Academy of Dermatology and Venereology: JEADV 23, 1123-1127, doi:10.1111/j.1468-3083.2009.03292.x (2009).
27 Braun, N., Covarrubias, R. & Major, A. Natural killer T cells and atherosclerosis: form and function meet pathogenesis. Journal of innate immunity 2, 316-324, doi: 10.1159/000296915 (2010).
28 Comstock, L. E. et al. Analysis of a capsular polysaccharide biosynthesis locus of *Bacteroides fragilis*. Infect Immun 67, 3525-3532 (1999).

OTHER EMBODIMENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A method comprising
   administering to a subject having or at risk of developing a condition characterized by increased invariant natural killer T (iNKT) cell numbers or activity an isolated immune inhibitory alpha-galactosylceramide in an effective amount to decrease iNKT cell numbers or activity,
   wherein the isolated alpha-galactosylceramide has the structure

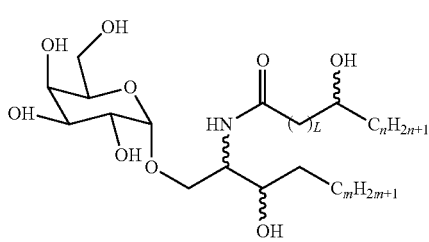

wherein m is any integer from 11 to 15, L is any integer from 0 to 2, and n+L is any integer from 13 to 17.

2. The method of claim 1, wherein the fatty acid or sphingosine chain length is 16, 17, 18 or 19 carbons.

3. The method of claim 1, wherein the fatty acid or sphingosine chain length is 17 carbons.

4. The method of claim 1, wherein each of the fatty acid and sphingosine chain lengths is 17 carbons.

5. The method of claim 1, wherein the alpha-galactosylceramide has a fatty acid or sphingosine chain that is branched.

6. The method of claim 5, wherein the fatty acid or sphingosine chain is branched at the omega-2 (iso) position or omega-3 (anteiso) position.

7. The method of claim 5, wherein the fatty acid or sphingosine chain comprises a terminal isomethyl or anteisomethyl group.

8. The method of claim 5, wherein each of the fatty acid or sphingosine chain comprises a terminal isomethyl or anteisomethyl group.

9. The method of claim 1, wherein the condition is an autoimmune disease.

10. The method of claim 1, wherein the condition is inflammatory bowel disease.

11. The method of claim 10, wherein the isolated alpha-galactosylceramide is administered to gut of the subject.

12. The method of claim 1, wherein the subject is human.

13. The method of claim 1, wherein the subject is administered another immunosuppressant.

14. The method of claim 1, wherein the alpha-galactosylceramide has the structure:

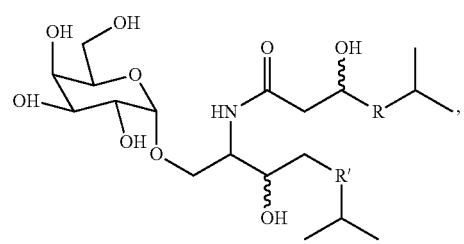

wherein R is defined as $C_nH_{2n}$, wherein R' is defined as $C_mH_{2m}$, wherein n is any integer from 10 to 13, and wherein m is any integer from 9 to 12.

15. The method of claim 1, wherein the alpha-galactosylceramide has the structure:

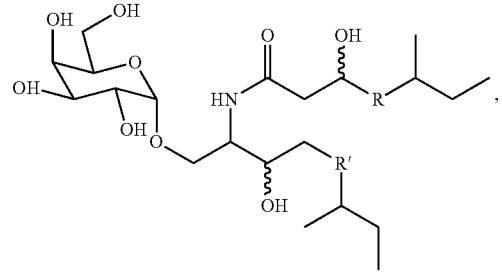

wherein R is defined as $C_nH_{2n}$, wherein R' is defined as $C_mH_{2m}$, wherein n is any integer from 10 to 13, and wherein m is any integer from 9 to 12.

16. The method of claim 1, wherein the fatty acid C3' position of the isolated alpha-galactosylceramide has
(a) R-chirality, or
(b) S-chirality, and
wherein the sphingosine C3 position has
(a) R-chirality, or
(b) S-chirality.

17. The method of claim 1, wherein the condition characterized by increased iNKT cell numbers or activity is an inflammatory condition or an autoimmune disease.

18. The method of claim 1, wherein the condition is:
(a) asthma;
(b) inflammatory bowel disease; or
(c) colitis.

* * * * *

UNITED STATES PATENT AND TRADEMARK OFFICE
CERTIFICATE OF CORRECTION

PATENT NO. : 10,329,315 B2
APPLICATION NO. : 14/435222
DATED : June 25, 2019
INVENTOR(S) : Dennis L. Kasper et al.

Page 1 of 1

It is certified that error appears in the above-identified patent and that said Letters Patent is hereby corrected as shown below:

In the Specification

At Column 1, Line 16 Should read:
FEDERALLY SPONSORED RESEARCH
"This invention was made with U.S. Government support under grant numbers AI090102 and DK102771 awarded by the National Institutes of Health. The U.S. Government has certain rights in this invention."

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*